US008927489B2

(12) United States Patent
Wahren et al.

(10) Patent No.: US 8,927,489 B2
(45) Date of Patent: Jan. 6, 2015

(54) SUSTAINED RELEASE PREPARATION OF PRO-INSULIN C-PEPTIDE

(75) Inventors: John Wahren, Stockholm (SE); Anders Carlsson, Stockholm (SE)

(73) Assignee: Cebix Incorporated, San Diego, CA (US)

( * ) Notice: Subject to any disclaimer, the term of this patent is extended or adjusted under 35 U.S.C. 154(b) by 1611 days.

(21) Appl. No.: 11/916,116

(22) PCT Filed: Jun. 2, 2006

(86) PCT No.: PCT/GB2006/001997
§ 371 (c)(1),
(2), (4) Date: Dec. 8, 2008

(87) PCT Pub. No.: WO2006/129095
PCT Pub. Date: Dec. 7, 2006

(65) Prior Publication Data
US 2009/0170761 A1 Jul. 2, 2009

(30) Foreign Application Priority Data
Jun. 2, 2005 (GB) .................................. 0511269.3

(51) Int. Cl.
*A61K 38/28* (2006.01)
*A61K 38/00* (2006.01)
*A61K 38/16* (2006.01)
*A61K 38/10* (2006.01)
*A61K 38/08* (2006.01)
*A61K 38/06* (2006.01)
*A61K 38/04* (2006.01)
*A61K 9/00* (2006.01)
*A61K 47/02* (2006.01)

(52) U.S. Cl.
CPC .............. *A61K 38/28* (2013.01); *A61K 9/0024* (2013.01); *A61K 9/0019* (2013.01); *A61K 47/02* (2013.01)
USPC ........... 514/5.9; 514/7.3; 514/21.3; 514/21.4; 514/21.5; 514/21.6; 514/21.8; 514/21.9; 530/303; 530/324; 530/326; 530/327; 530/328; 530/329; 530/330

(58) Field of Classification Search
CPC ....... A61K 38/28; A61K 38/17; A61K 38/02; A61K 38/04; A61K 38/08; A61K 38/10; A61K 38/1709; A61K 38/00; C07K 14/62; C07K 14/435; C07K 7/08; C07K 7/06
See application file for complete search history.

(56) References Cited

U.S. PATENT DOCUMENTS

| 2,143,590 A | 1/1939 | Scott |
| 2,882,203 A | 4/1959 | Petersen et al. |
| 3,678,027 A | 7/1972 | De Jager et al. |
| 3,852,422 A | 12/1974 | Donini |
| 3,869,549 A | 3/1975 | Geller |
| 5,595,760 A | 1/1997 | Cherif-Cheikh |
| 6,503,534 B1 | 1/2003 | Pellet et al. |
| 8,691,755 B2 * | 4/2014 | Barrack et al. ................. 514/3.2 |
| 2003/0044463 A1 | 3/2003 | Deghenghi et al. |
| 2003/0072803 A1 | 4/2003 | Goldenberg |
| 2004/0053817 A1 * | 3/2004 | Mohr et al. ....................... 514/3 |
| 2006/0025524 A1 | 2/2006 | Schneider |
| 2006/0045869 A1 * | 3/2006 | Meezan et al. ............... 424/85.4 |

FOREIGN PATENT DOCUMENTS

| EP | 177478 B1 | 4/1991 |
| EP | 0510913 B1 | 7/2000 |
| EP | 0619322 B1 | 12/2005 |
| GB | 2104382 A | 3/1983 |
| WO | WO 95/21622 A1 | 8/1995 |
| WO | WO 96/20005 A1 | 7/1996 |
| WO | 0215937 A2 | 2/2002 |
| WO | WO 02/15937 A2 | 2/2002 |
| WO | 0238129 A2 | 5/2002 |
| WO | WO 02/38129 A2 | 5/2002 |
| WO | WO 03/006049 A1 | 1/2003 |
| WO | WO 03/075887 A1 | 9/2003 |
| WO | WO 2004/016647 A2 | 2/2004 |
| WO | 06076042 A2 | 7/2006 |
| WO | 2006129095 A3 | 12/2006 |

OTHER PUBLICATIONS

Lockwood et al. 2002. Biomacromolecules 3:1225-1232.*
International Preliminary Report on Patentability, Creative Peptides Sweden AB, PCT/GB2006/001997, Dec. 6, 2007.
Johansson, B.L. et al. (2000) "Beneficial effects of C-peptide on incipient nephropathy and neuropathy in patients with Type 1 diabetes mellitus" Diabetic Medicine, John Wiley & Sons, Ltd, 17: 181-189.
Wong, G. et al. (1994) "Formulation and sterilization of a sustained release delivery system for a gel forming peptide" Pharmaceutical Research 11:S312, XP009079051.
Wong, G. et al. (1994) "Measurement of surface activities and preformulation studies on a gel forming peptide" Pharmaceutical research 11:S226, XP009079052.
Gray, R. et al. (1994) "Dissolution studies on the sustained-release characteristics of a gel-forming decapeptide" Pharmaceutical Research 11:S88, XP009079050.
Johansson, B., et al, Beneficial Effects of C-peptide on incipient nephropathy and neuropathy in patients with Type 1 diabetes mellitus, Diabetic medicine, 2000, 181-189, 17.
Gray, Ronda A., et al, Biotec 2069, Dissolution Studies on the Sustained-Release Characteristics of a Gel-forming Decapetide, Pharmaceutical Development, Reproductive Research, The R.W. Johnson Pharmaceutical Research Institute, Raritan, NJ 08869, 1994.

(Continued)

*Primary Examiner* — Shulamith H Shafer
(74) *Attorney, Agent, or Firm* — Morrison & Foerster LLP

(57) ABSTRACT

The present invention provides a pharmaceutical composition for the sustained release of C-peptide. The composition is in the form of a gel containing C-peptide. The gel formation is achieved by the adjustment of pH of the composition and/or by addition of divalent metal ions. The composition does not include any other gel-forming agents. Methods for producing the composition, medical uses of the composition and products containing two or more gel compositions as a combined preparation are also encompassed.

23 Claims, 8 Drawing Sheets

(56) References Cited

OTHER PUBLICATIONS

Wong, George K., et al, PDD 7207, Measurement of Surface Activities and Preformulation Studies on a Gel Forming Peptide, Pharmaceutical Development, The R.W. Johnson Pharmaceutical Research Institute, Raritan, NJ 08869, 1994.

Wong, George K., et al, PDD 7550, Formulation and Sterilization of a Sustained Release Delivery System for a Gel Forming Peptide Pharmaceutical Development, The R.W. Johnson Pharmaceutical Research Institute, Raritan, NJ 08869, 1994.

Faber, O.K. et al. 1978 "Kinetics of human C-peptide in man" *Diabetes* 27:207-209.

Henriksson, M. et al. 2000 "Unordered structure of proinsulin C-peptide in aqueous solution and in the presence of lipid vesicles" *Cell and Molec Life Sci* 57:337-342.

Ido, Y. et al. 1997 "Prevention of vascular and neural dysfunction in diabetic rats by C-peptide" *Science* 277:563-566.

Kitamura, T. et al. 2001 "Proinsulin C-peptide rapidly stimulates mitogen-activated protein kinases in Swiss 3T3 fibroblasts: requirement of protein kinase C, phosphoinositide 3-kinase and pertussis toxin-sensitive G-protein" *Biochem J* 355:123-129.

Melles, E. et al. 2003 "Proinsulin C-peptide and its C-terminal pentapeptide: degradation in human serum and Schiff base formation with subsequent $CO_2$ incorporation" *Cell and Molec Life Sci* 60:1019-1025.

Ohtomo, Y. et al. 1996 "C-peptide stimulates rat renal tubular $Na^+$, $K^+$-ATPase activity in synergism with neuropeptide Y" *Diabetologia* 39:199-205.

Ohtomo, Y. et al. 1998 "Differential effects of proinsulin C-peptide fragments on $Na^+$, $K^+$-ATPase activity of renal tubule segments" *Diabetologia* 41:287-291.

Pramanik, A. et al. 2001 "C-peptide binding to human cell membranes: importance of Glu27" *Biochem and Biophys Res Comm* 284:94-98.

Rigler, R. et al. 1999 "Specific binding of proinsulin C-peptide to human cell membranes" *Proc Natl Acad Sci USA* 96:13318-13323.

Shafqat, J. et al. 2002 "Proinsulin C-peptide and its analogues induce intracellular $Ca^{2+}$ increases in human renal tubular cells" *Cell and Molec Life Sci* 59:1185-1189.

Wahren, J. and Johansson, B.L. "New aspects of C-peptide physiology" *Horm Metab Res* 30:A2-A5, 1998.

Wahren, J. et al. 2000 "Role of C-peptide in human physiology" *Am J Physiol Endocrinol Metab* 278:E759-E768.

Wallerath, T. et al. "Stimulation of endothelial nitric oxide synthase by proinsulin C-peptide" *Nitric Oxide* 9:95-102, 2003.

Zavaroni, I. et al. 1987 "Renal metabolism of C-peptide in man" *J Clin Endocrinol and Metab* 65:494-498.

\* cited by examiner

| Proinsulin | C-peptide | |
|---|---|---|
| Ins_Human | EAEDLQVGQVELGGGPGAGSLQPLALEGSLQ | (SEQ ID NO. 1) |
| Ins_Pantr (Chimpanzee) | EAEDLQVGQVELGGGPGAGSLQPLALEGSLQ | (SEQ ID NO. 2) |
| Ins_Aotr (Night monkey) | EAEDLQVGQVELGGGSITGSLPPLEGPMQ | (SEQ ID NO. 3) |
| Ins_Macpa (Crabeatingmaoaque) | EAEDPQVGQVELCSGGPGAGSLQPLALEGSLQ | (SEQ ID NO. 4) |
| Ins_Cerab (Green monkey) | EAEDPQVGQVELGGGPGAGSLQPLALEGSLQ | (SEQ ID NO. 5) |
| Ins_Pig | EAENPQAGAVELGGGLGGLQALALEGPPQ | (SEQ ID NO. 6) |
| Ins_Boven | EVEGPQVGALELAGGPGAGGLEGPPQ | (SEQ ID NO. 7) |
| Ins_Horse | EAEDPQVGEVELGGGPGLGGLQPLALAGPQQ | (SEQ ID NO. 8) |
| Ins_sheep | EVEGPQVGALELAGGPGAGGLEGPPQ | (SEQ ID NO. 9) |
| Ins_Canpa (dog) | EVEDLQVRDVELAGAPGEGGLQPLALEGALQ | (SEQ ID NO. 10) |
| Ins_Rabbit | EVEELQVGQAELGGGPGAGGLQPSALELALQ | (SEQ ID NO. 11) |
| Ins_1_Rat | EVEDPQYPQLEGGPEAGDLQTLALEVARQ | (SEQ ID NO. 12) |
| Ins2_Rat | EVEDPQVAQLELGGGPGAGDLQTLALEVARQ | (SEQ ID NO. 13) |
| Ins_Rodsp (rodent sp) | EVEDPQVGQVELGAGPGAGSEQTLALEVARQ | (SEQ ID NO.14) |
| Insi_mouse | EVEDPQVEQLELGGSPGDLQTLALEVARQ | (SEQ ID NO. 15) |
| Ins2_Mouse | EVEDPQVAQLELGGGPGAGDLQTLALEVAQQ | (SEQ ID NO. 16) |
| Ins_Caypo (guinea pig) | ELEDPQYEQTELGMGLGAGGLQPLALEMALQ | (SEQ ID NO. 17) |
| Ins_Crib | GVEDPQVAQLELGGGPGADDLQTLALEVAQQ | (SEQ ID NO. 18) |
| Ins_Psaob | GYDDPQMPQLEGGSPGAGDLRALALEVARQ | (SEQ ID NO. 19) |
| Ins_Ocide | ELEDLQVEQAELGLEAGGLQPSALEMILQ | (SEQ ID NO. 20) |
| Q62543 (western wild mouse) | GGPGAGDLQTLALEVAQQ | (SEQ ID NO. 21) |
| Q62542 (western wild mouse) | GSPGDLQTLALEVARQ | (SEQ ID NO. 22) |
| Ins_Anapl (domestic duck) | DVEQPLVNGPLKGEVGELPPQHEEYQXX | (SEQ ID NO. 23) |
| Ins_Chick (chicken) | DVEQPLYSSPLKGEAGYLPPQQEEYEKV | (SEQ ID NO. 24) |

FIG. 1

```
                        SEQUENCE LISTING

<160> NUMBER OF SEQ ID NOS: 31

<210> SEQ ID NO 1
<211> LENGTH: 31
<212> TYPE: PRT
<213> ORGANISM: Homo sapiens
```

-continued

<400> SEQUENCE: 1

Glu Ala Glu Asp Leu Gln Val Gly Gln Val Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 2
<211> LENGTH: 31
<212> TYPE: PRT
<213> ORGANISM: Pan troglodytes

<400> SEQUENCE: 2

Glu Ala Glu Asp Leu Gln Val Gly Gln Val Glu Leu Gly Gly Pro
1               5                   10                  15

Gly Ala Gly Ser Leu Gln Pro Leu Ala Leu Glu Gly Ser Leu Gln
            20                  25                  30

<210> SEQ ID NO 3
<211> LENGTH: 29
<212> TYPE: PRT
<213> ORGANISM: Aotus trivirgatus

<400> SEQUENCE: 3

Glu Ala Glu Asp Leu Gln Val Gly Gln Val Glu Leu Gly Gly Ser
1               5                   10                  15

Ile Thr Gly Ser Leu Pro Pro Leu Glu Gly Pro Met Gln
            20                  25

<210> SEQ ID NO 4
<211> LENGTH: 32
<212> TYPE: PRT
<213> ORGANISM: Macaca fasicularis

<400> SEQUENCE: 4

Glu Ala Glu Asp Pro Gln Val Gly Gln Val Glu Leu Cys Ser Gly Gly
1               5                   10                  15

Pro Gly Ala Gly Ser Leu Gln Pro Leu Ala Leu Glu Gly Ser Leu Gln
            20                  25                  30

<210> SEQ ID NO 5
<211> LENGTH: 31
<212> TYPE: PRT
<213> ORGANISM: Cercopithecus aethiops

<400> SEQUENCE: 5

Glu Ala Glu Asp Pro Gln Val Gly Gln Val Glu Leu Gly Gly Pro
1               5                   10                  15

Gly Ala Gly Ser Leu Gln Pro Leu Ala Leu Glu Gly Ser Leu Gln
            20                  25                  30

<210> SEQ ID NO 6
<211> LENGTH: 29
<212> TYPE: PRT
<213> ORGANISM: Sus domestica

<400> SEQUENCE: 6

Glu Ala Glu Asn Pro Gln Ala Gly Ala Val Glu Leu Gly Gly Leu
1               5                   10                  15

Gly Gly Leu Gln Ala Leu Ala Leu Glu Gly Pro Pro Gln
            20                  25

-continued

```
<210> SEQ ID NO 7
<211> LENGTH: 26
<212> TYPE: PRT
<213> ORGANISM: Bos taurus

<400> SEQUENCE: 7

Glu Val Glu Gly Pro Gln Val Gly Ala Leu Glu Leu Ala Gly Gly Pro
1               5                   10                  15

Gly Ala Gly Gly Leu Glu Gly Pro Pro Gln
            20                  25

<210> SEQ ID NO 8
<211> LENGTH: 31
<212> TYPE: PRT
<213> ORGANISM: Equus caballus

<400> SEQUENCE: 8

Glu Ala Glu Asp Pro Gln Val Gly Glu Val Glu Leu Gly Gly Gly Pro
1               5                   10                  15

Gly Leu Gly Gly Leu Gln Pro Leu Ala Leu Ala Gly Pro Gln Gln
            20                  25                  30

<210> SEQ ID NO 9
<211> LENGTH: 26
<212> TYPE: PRT
<213> ORGANISM: Ovis aries

<400> SEQUENCE: 9

Glu Val Glu Gly Pro Gln Val Gly Ala Leu Glu Leu Ala Gly Gly Pro
1               5                   10                  15

Gly Ala Gly Gly Leu Glu Gly Pro Pro Gln
            20                  25

<210> SEQ ID NO 10
<211> LENGTH: 31
<212> TYPE: PRT
<213> ORGANISM: Canis lupus familiaris

<400> SEQUENCE: 10

Glu Val Glu Asp Leu Gln Val Arg Asp Val Glu Leu Ala Gly Ala Pro
1               5                   10                  15

Gly Glu Gly Gly Leu Gln Pro Leu Ala Leu Gly Ala Leu Gln
            20                  25                  30

<210> SEQ ID NO 11
<211> LENGTH: 31
<212> TYPE: PRT
<213> ORGANISM: Oryctolagus cuniculus

<400> SEQUENCE: 11

Glu Val Glu Glu Leu Gln Val Gly Gln Ala Glu Leu Gly Gly Gly Pro
1               5                   10                  15

Gly Ala Gly Gly Leu Gln Pro Ser Ala Leu Glu Leu Ala Leu Gln
            20                  25                  30

<210> SEQ ID NO 12
<211> LENGTH: 29
<212> TYPE: PRT
<213> ORGANISM: Rattus norvegicus

<400> SEQUENCE: 12

Glu Val Glu Asp Pro Gln Tyr Pro Gln Leu Glu Gly Gly Pro Glu Ala
```

```
                1               5                   10                  15

Gly Asp Leu Gln Thr Leu Ala Leu Glu Val Ala Arg Gln
            20                  25

<210> SEQ ID NO 13
<211> LENGTH: 31
<212> TYPE: PRT
<213> ORGANISM: Rattus norvegicus

<400> SEQUENCE: 13

Glu Val Glu Asp Pro Gln Val Ala Gln Leu Glu Leu Gly Gly Gly Pro
1               5                   10                  15

Gly Ala Gly Asp Leu Gln Thr Leu Ala Leu Glu Val Ala Arg Gln
            20                  25                  30

<210> SEQ ID NO 14
<211> LENGTH: 31
<212> TYPE: PRT
<213> ORGANISM: Rodentia spp.

<400> SEQUENCE: 14

Glu Val Glu Asp Pro Gln Val Gly Gln Val Glu Leu Gly Ala Gly Pro
1               5                   10                  15

Gly Ala Gly Ser Glu Gln Thr Leu Ala Leu Glu Val Ala Arg Gln
            20                  25                  30

<210> SEQ ID NO 15
<211> LENGTH: 29
<212> TYPE: PRT
<213> ORGANISM: Mus musculus

<400> SEQUENCE: 15

Glu Val Glu Asp Pro Gln Val Glu Gln Leu Glu Leu Gly Gly Ser Pro
1               5                   10                  15

Gly Asp Leu Gln Thr Leu Ala Leu Glu Val Ala Arg Gln
            20                  25

<210> SEQ ID NO 16
<211> LENGTH: 31
<212> TYPE: PRT
<213> ORGANISM: Mus musculus

<400> SEQUENCE: 16

Glu Val Glu Asp Pro Gln Val Ala Gln Leu Glu Leu Gly Gly Gly Pro
1               5                   10                  15

Gly Ala Gly Asp Leu Gln Thr Leu Ala Leu Glu Val Ala Gln Gln
            20                  25                  30

<210> SEQ ID NO 17
<211> LENGTH: 31
<212> TYPE: PRT
<213> ORGANISM: Cavia porcellus

<400> SEQUENCE: 17

Glu Leu Glu Asp Pro Gln Tyr Glu Gln Thr Glu Leu Gly Met Gly Leu
1               5                   10                  15

Gly Ala Gly Gly Leu Gln Pro Leu Ala Leu Glu Met Ala Leu Gln
            20                  25                  30

<210> SEQ ID NO 18
<211> LENGTH: 31
<212> TYPE: PRT
```

<213> ORGANISM: Cricetulus longicaudatus

<400> SEQUENCE: 18

Gly Val Glu Asp Pro Gln Val Ala Gln Leu Glu Leu Gly Gly Gly Pro
1               5                   10                  15

Gly Ala Asp Asp Leu Gln Thr Leu Ala Leu Glu Val Ala Gln Gln
            20                  25                  30

<210> SEQ ID NO 19
<211> LENGTH: 31
<212> TYPE: PRT
<213> ORGANISM: Psammomys obesus

<400> SEQUENCE: 19

Gly Tyr Asp Asp Pro Gln Met Pro Gln Leu Glu Leu Gly Gly Ser Pro
1               5                   10                  15

Gly Ala Gly Asp Leu Arg Ala Leu Ala Leu Glu Val Ala Arg Gln
            20                  25                  30

<210> SEQ ID NO 20
<211> LENGTH: 29
<212> TYPE: PRT
<213> ORGANISM: Octodon degus

<400> SEQUENCE: 20

Glu Leu Glu Asp Leu Gln Val Glu Gln Ala Leu Gly Leu Glu Ala
1               5                   10                  15

Gly Gly Leu Gln Pro Ser Ala Leu Glu Met Ile Leu Gln
            20                  25

<210> SEQ ID NO 21
<211> LENGTH: 18
<212> TYPE: PRT
<213> ORGANISM: Mus spretus

<400> SEQUENCE: 21

Gly Gly Pro Gly Ala Gly Asp Leu Gln Thr Leu Ala Leu Glu Val Ala
1               5                   10                  15

Gln Gln

<210> SEQ ID NO 22
<211> LENGTH: 16
<212> TYPE: PRT
<213> ORGANISM: Mus spretus

<400> SEQUENCE: 22

Gly Ser Pro Gly Asp Leu Gln Thr Leu Ala Leu Glu Val Ala Arg Gln
1               5                   10                  15

<210> SEQ ID NO 23
<211> LENGTH: 28
<212> TYPE: PRT
<213> ORGANISM: Anas platyrhynchos
<220> FEATURE:
<221> NAME/KEY: misc_feature
<222> LOCATION: (27)..(28)
<223> OTHER INFORMATION: Xaa can be any naturally occurring amino acid

<400> SEQUENCE: 23

Asp Val Glu Gln Pro Leu Val Asn Gly Pro Leu Lys Gly Glu Val Gly
1               5                   10                  15

Glu Leu Pro Pro Gln His Glu Glu Tyr Gln Xaa Xaa
            20                  25

```
<210> SEQ ID NO 24
<211> LENGTH: 28
<212> TYPE: PRT
<213> ORGANISM: Gallus gallus

<400> SEQUENCE: 24

Asp Val Glu Gln Pro Leu Tyr Ser Ser Pro Leu Lys Gly Glu Ala Gly
1               5                   10                  15

Tyr Leu Pro Pro Gln Gln Glu Glu Tyr Glu Lys Val
            20                  25

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide

<400> SEQUENCE: 25

Glu Gly Ser Leu Gln
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Glu Leu Gly Gly Gly Pro Gly Ala Gly
1               5

<210> SEQ ID NO 27
<211> LENGTH: 4
<212> TYPE: PRT
<213> ORGANISM: Artificial Sequence
<220> FEATURE:
<223> OTHER INFORMATION: Synthetic peptide

<400> SEQUENCE: 27

Glu Leu Gly Gly
1

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide

<400> SEQUENCE: 28

Glu Leu Gly Gly Gly Pro
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic peptide

<400> SEQUENCE: 29

Glu Gly Pro Gly Ala
1               5
```

```
<210> SEQ ID NO 30
<211> LENGTH: 4
<212> TYPE: PRT
<213> ORGANISM: Artificial Sequence
<220> FEATURE:
<223> OTHER INFORMATION: synthetic peptide

<400> SEQUENCE: 30

Gly Ser Leu Gln
1

<210> SEQ ID NO 31
<211> LENGTH: 12
<212> TYPE: PRT
<213> ORGANISM: Artificial Sequence
<220> FEATURE:
<223> OTHER INFORMATION: Sythetic peptide

<400> SEQUENCE: 31

Glu Ala Glu Asp Leu Gln Val Gly Ala Val Glu Leu
1               5                   10
```

SUSTAINED RELEASE PREPARATION OF PRO-INSULIN C-PEPTIDE

CROSS-REFERENCE TO RELATED APPLICATIONS

This Application was filed under 35 U.S.C. §365 and claims priority to International Application Number PCT/GB2006/001997 filed on Jun. 2, 2006, and to GB Application No. 0511269.3 filed Jun. 2, 2005.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The present invention relates to preparations of proinsulin C-peptide. The preparations are in the form of a gel and allow for sustained release of C-peptide over a length of time. Such preparations may be used in the treatment of diabetes and/or diabetic complications.

2. Description of Related Art

Insulin-dependent diabetes mellitus (IDDM), generally synonymous with type 1 diabetes, is the classical, life-threatening form of diabetes, the treatment of which was revolutionized by the discovery of insulin in 1922. The prevalence of IDDM is unfortunately widespread throughout much of the world and hence IDDM represents a serious condition with a significant drain on health resources.

The etiology of IDDM is multifactorial and not yet entirely clear. However it is characterised by a partial or complete destruction of the pancreatic beta cells. In the acute phase of IDDM insulin deficiency it is thus the dominating pathophysiological feature.

After starting insulin treatment many patients enjoy good blood glucose control with only small doses of insulin. There is an early phase, the "honeymoon period", which may last a few months to a year and which probably reflects a partial recovery of beta cell function. This is, however, a temporary stage and ultimately, the progressive destruction of the beta cells leads to complete cessation of insulin secretion and increasing requirements for exogenous insulin.

While the short term effects of hypoinsulinemia in the acute phase of IDDM can be well controlled by insulin administration, the long term natural history of IDDM is darkened by the appearance in many patients of potentially serious complications known as late, or late onset complications. These include the specifically diabetic problems of nephropathy, retinopathy and neuropathy. These conditions are often referred to as microvascular complications even though microvascular alterations are not the only cause. Atherosclerotic disease of the large arteries, particularly the coronary arteries and the arteries of the lower extremities, may also occur.

Nephropathy develops in approximately 35% of IDDM patients, particularly in male patients and in those with onset of the disease before the age of 15 years. Diabetic nephropathy is characterized by persistent albuminuria secondary to glomerular capillary damage, a progressive reduction of the glomerular filtration rate and eventually, end stage renal failure.

The prevalence of diabetic retinopathy is highest among young-onset IDDM patients and it increases with the duration of the disease. Proliferative retinopathy is generally present in about 25% of the patients after 15 years duration and in over 50% after 20 years. The earliest lesion of diabetic retinopathy is a thickening of the capillary basement membrane, followed by capillary dilation and leakage and formation of microaneurysms. Subsequently, occlusion of retinal vessels occurs resulting in hypoperfusion of parts of the retina, oedema, bleeding and formation of new vessels as well as progressive loss of vision.

Diabetic neuropathy includes a wide variety of disturbances of somatic and autonomic nervous function. Sensory neuropathy may cause progressive loss of sensation or, alternatively, result in unpleasant sensations, often pain, in the legs or feet. Motor neuropathy is usually accompanied by muscle wasting and weakness. Nerve biopsies generally show axonal degeneration, demyelination and abnormalities of the vasa nervorum. Neurophysiological studies indicate reduced motor and sensory nerve conduction velocities. Autonomic neuropathy afflicts some 40% of the patients with IDDM of more than 15 years duration. It may evolve through defects in thermoregulation, impotence and bladder dysfunction followed by cardiovascular reflex abnormalities. Late manifestations may include generalized sweating disorders, postural hypotension, gastrointestinal problems and reduced awareness of hypoglycemia. The latter symptom has grave clinical implications.

A number of theories have been advanced with regard to possible mechanism(s) involved in the pathogenesis of the different diabetic complications, but this has not yet been fully elucidated. Metabolic factors may be of importance and it has been shown that good metabolic control is accompanied by significantly reduced incidence of complications of all types. Nevertheless, after 7-10 years of good metabolic control, as many as 15-25% of the patients show signs of beginning nephropathy, 10-25% have symptoms of retinopathy and 15-20% show delayed nerve conduction velocity indicating neuropathy. With longer duration of the disease the incidence of complications increases further. There is thus a significant clinical need for the control and management of these diabetic complications.

Proinsulin C-peptide is a part of the proinsulin molecule which, in turn, is a precursor to insulin formed in the beta cells of the pancreas. For a long time it was believed that C-peptide (known variously as C-peptide or proinsulin C-peptide) had no role other than as a structural component of proinsulin, facilitating correct folding of the insulin part. However, it has in more recent years been recognised that C-peptide has a physiological role as a hormone in its own right (Wahren et al., (2000), Am. J. Physiol. Endocrinol. Metab, 278, E759-E768). In diabetic patients, it alleviates renal dysfunction, improves blood flow in several tissues, ameliorates nerve functional impairments and is believed to delay or prevent the onset of late complications (Wahren et al., (2000) supra; Wahren and Johansson (1998), Horm. Metab. Res. 30, A2-A5). Indeed, C-peptide has been proposed for use in the treatment of diabetes in EP 132769 and in SE460334 for use in combination with insulin in the treatment of diabetes and prevention of diabetic complications.

Proinsulin, or large parts of it, is known in 37 different variants, representing 33 different species, ranging from Atlantic hagfish, Myxine glutinosa, to human. Whilst the insulin segments (i.e. the A and B chains of proinsulin) are well conserved between species, C-peptide is much more highly variable, showing not only sequence variation, but also several internal deletions, making the length of C-peptide variable (see FIG. 1).

Human C-peptide is a 31 amino acid peptide having the following sequence:

EAEDLQVGQVELGGGPGAGSLQPLALEGSLQ. (SEQ ID. NO. 1)

C-peptide can be ascribed a tripartite overall structure, with more conserved N- and C-terminal segments and a more variable mid-sequence, or internal, portion. Thus, in the case of human C-peptide the N-terminal segment can be regarded as residues 1-12, the mid-portion as residues 13-25, and the C-terminal segment as residues 26-31.

The C-terminal pentapeptide fragment of C-peptide has been shown to have similar physiological and molecular effects to C-peptide itself, suggesting that this segment is an essential part of C-peptide (Wahren et al., 2000, supra; Rigler et al., 1999, PNAS USA 96, 13318-13323; Ohtomo et al., 1998, Diabetologia 41, 287-291; Pramanik et al., 2001, BBRC 284, 94-98; Shafqat et al, 2002, Cell Mol. Life. Sci., 59, 1185-1189). WO 98/13384 proposes the use of this C-terminal pentapeptide, and other C-terminally located peptide fragments of C-peptide in the treatment of diabetes and diabetic complications. The mid-sequence portion also has been shown to have molecular and physiological effects (see e.g. Ido et al. (1997, Science 277, 563-566) and Ohtomo et al., (1998), supra) and has also been proposed in WO 98/13384 to have clinical utility. Ido et al., have speculated that the mid-portion may mediate its effects through membrane interactions, although this is still to be confirmed and is not supported by other studies. The N-terminal segment of C-peptide although not active on its own, has also recently been shown to be functionally important and to contribute to C-peptide activity. Accordingly, various N-terminal fragments and derivatives of C-peptide, including in particular variants of C-peptide modified in the N-terminal region, have also been proposed in WO 2004/016647 to have therapeutic utility.

C-peptide thus appears to be a somewhat "complex" molecule, which may exert its effects by a variety of different mechanisms, including possibly via interaction with more than one receptor and/or more than one signalling pathway. Direct membranotropic mechanisms may also be involved although, as mentioned above, this is yet to be conclusively established. Thus, not only C-peptide itself (i.e. an intact native or wild-type C-peptide) but also various C-peptide fragments and modified variants or analogues thereof have therapeutic potential in the treatment and/or prevention of diabetes and/or diabetic complications. The use or potential use of all such C-peptides, and fragments and derivatives thereof is referred to herein as "C-peptide therapy".

C-peptide is known, however, to have a relatively short half-life in the body (specifically in the circulation or plasma). The major degradation and removal of C-peptide takes place in the kidneys (Faber et al., Diabetes, 27, 207-209, 1978; Zavaroni et al., J. Clin. Endocrinol. Metab., 65, 494-498, 1987), although little is known in the prior art concerning the proteolytic enzymes involved and the mode of degradation.

Studies have shown that both C-peptide and its C-terminal pentapeptide are degraded in serum, with a longer half-life for intact C-peptide than for the C-terminal pentapeptide. Preliminary evidence suggests that the two peptides may be degraded in different ways in the serum. (Melles et al., Cell. Mol. Life. Sci., 60, 1019-1025, 2003).

The in vivo half life of C-peptide circulating in blood has been reported as approximately 30 minutes (as compared to 4-5 minutes for insulin), and that of the C-terminal pentapeptide is believed to be even shorter. Studies have shown that a dose of C-peptide injected into a rat would be expected to have disappeared entirely from circulation within 2-3 hours. Thus, in studying C-peptide physiological activity or in C-peptide therapy, it has been customary to administer C-peptide in several daily doses or to use a continuous dose. Similarly insulin, which is derived from the same prohormone (proinsulin) as C-peptide requires administration 3-5 times daily.

Hence, formulations of C-peptide which require fewer daily administrations would have clear clinical benefits. In WO 02/38129, a delayed release formulation of C-peptide is described, where C-peptide is present in an absorbable matrix designed to slow down the release of the peptide after administration to the patient.

The present invention is directed towards the aim of providing a longer lasting treatment and in particular towards providing a sustained release formulation of C-peptide. In this regard, the inventors have surprisingly found that C-peptide can form a gel under particular conditions. In particular, it has been found that a C-peptide composition may be transformed into a gellous state when combined with metal ions and/or by adjusting the pH of the composition. It is proposed that by using a C-peptide composition in such a gellous state (i.e. in the form of a gel) a sustained release formulation may be obtained, which allows for the sustained release of the C-peptide over a period of time after administration in vivo.

Thus, experiments have been conducted which show that such a gel composition may release both the C-peptide, and the metal ion (when present) over time in a manner controlled by the composition of the gel. This strongly indicates that the gel can be used as a sustained release formulation of C-peptide. The beneficial features of the present invention include the simplicity and the ease with which the gels can be made, the fact that few ingredients are required, and the long shelf life of the gels.

BRIEF SUMMARY OF THE INVENTION

Thus, in one aspect the present invention provides a pharmaceutical composition for the sustained release of C-peptide, said composition being in the form of a gel comprising C-peptide, wherein gel formation is achieved by the adjustment of pH of the composition, and/or by addition of divalent metal ions, and wherein said composition does not include any other gel-forming agents.

DETAILED DESCRIPTION OF THE INVENTION

The term "sustained release" as used herein denotes a pharmaceutical preparation from which the active substance is released in a therapeutically-relevant amount under physiological conditions over a prolonged period of time. This may be a period of at least 5, 6, 7, 8, 10, 12, 15, 18, 20, 22 or 24 hours. Preferred sustained-release formulations are those from which C-peptide is released in therapeutically relevant amounts over a period of at least 12 or 24 hours or at least 1, 2, 3, 4, 5, 6 or 7 days. The period of release may vary depending upon the nature of the gel, and how it was formed, concentration of C-peptide, concentration of metal ions, pH of the composition etc. Thus, the possibility of a wide range of periods of "sustained release" is encompassed, ranging from several hours to a number of days or weeks. Sustained release compositions may be formed which release C-peptide over a period of hours (e.g. 5 to 7 hours or 6 to 7 hours, 8 to 24 hours or 8 to 12 hours or 12 to 24 hours) and hence which may be administered to a patient on a once- or twice- or thrice-daily basis, or which release C-peptide over a longer period of time, for example a number or days, and hence which may be administered once every few days, e.g. once every 2, 3, 4, 5 or 6 days or on a once-weekly or twice-weekly basis. With appropriate adjustment of the gel-forming conditions, gels may also be formed which release C-peptide very slowly over a longer period of time, for example over at least 10, 12, 14, 16, 18, 20 or 21 days or longer.

A therapeutically relevant "release" may conveniently be measured in vivo by measuring the circulating plasma concentration of C-peptide. Any increase over the patient's basal circulating C-peptide plasma concentration (as measured prior to commencement of treatment) may be therapeutically relevant. However, typically a "therapeutically relevant" C-peptide plasma concentration may exceed 0.5 ng/ml (0.15 nM), and preferably it will exceed 0.7 ng/ml, e.g. about 1 ng/ml (0.3 nM). In typical pharmacokinetic profiles, an initial burst in release of C-peptide may be followed by a prolonged phase of sustained release. However, the term "sustained release" is not intended to limit to any particular kind of release profile, or any pattern of release, be it with an initial burst in release or not, or steady constant levels of release or not, and all patterns of sustained release are covered.

The term "gel" as used herein is defined generally as any colloidal system comprising a solid and a liquid phase which exists as solid or semi-solid mass. A gel may thus be viewed as a colloid in which the disperse phase has combined with the dispersion medium to produce a solid or semi-solid material. The term thus includes any preparation of C-peptide which has been transformed from a liquid to a gellous state (e.g. from a solution). A gel according to the present invention may include any gellous precipitate or macroscopic structure with a gel-like appearance and properties. The C-peptide solution prior to transformation may exist as a colloidal solution wherein the C-peptide and optionally metal ions (or metal salt) if present is dispersed.

Hence, during gel formation the viscosity of the composition increases and the composition transforms from a liquid (preferably from a solution) to a semi-solid or solid state, i.e. the composition transforms from a low viscosity state to a higher viscosity state.

Preferably, the gel has a dynamic viscosity at 20° C. of at least $y \cdot 10^{-3}$ $Ns/m^2$, y being 2.5 or more, preferably about 5 more, more preferable about 10 or more, most preferably about 30 or more.

C-peptide has a number of negatively charged amino acid side chains and hence in solution is a negatively charged molecule. Whilst not wishing to be bound by theory, the gel which is formed by exposure to divalent metal ions may be characterised as a polyelectrolyte complex.

Depending on how it is formed, the conditions and/or concentrations used etc., the gel which is obtained may exhibit different characteristics or properties. Thus gels may be formed with differing degrees of rigidity (or stiffness), ranging from semi-solid gels to highly rigid (stiff) gels.

The sensitivity to shear of the gel may also vary, and this may be (but need not be) in parallel to the rigidity (stiffness). Thus, a stiff gel may be formed which is only sensitive to high shear (for example vortex mixing at high speed, 2500 rpm). Alternatively, gels may be formed which are sensitive to shear, for example low shear such as shaking or swirling of the tube containing the gel. At the other end of the spectrum, gels may be obtained which are not sensitive to shear. Such gels cannot be liquefied or disrupted. Thus a spectrum of sensitivity to shear may be obtained, depending on the conditions employed to make the gel.

Thixotropic gels may also be obtained, which may be liquefied by applying shear, and which re-solidify when released from the shear source, for example when left standing.

It is preferred for the gels of the invention to have resistance to low shear at least (i.e. not to be disrupted by low shear at least), for example to be sensitive to (or disrupted by) high shear only, or to be shear-resistant (not sensitive to or disrupted by shear), although this is not essential. High shear is defined as vortex mixing at 2500 rpm or above. Low shear is defined as simple shaking or vortex shaking at 500 rpm or below. Thixotropic gels are also preferred. The sensitivity of the gel to shear can be reduced by the removal of excess ions, for example by dialysis.

The opacity of the gel may also vary, ranging from clear to opaque. Gels of intermediate "opacity" may be obtained which may be irregular or not homogeneous with respect to opacity As described in more detail below, the gels may take varying lengths of time to form, depending on the conditions and method used to form the gel, concentrations of reagents etc. This may vary from hours (e.g. 1 to 24 hours, e.g. 3 to 24 or 6 to 24 hours) or days (e.g. 1 to 11 days or 1 to 12, or 1 to 10, or 1 to 8 or 1 to 6 days, or 1, 2, 3, 4, 5, 6, 7, 8, 9, 10, 11, 12, 13 or 14 days, or more), or possibly even several weeks (e.g. 1 to 5 weeks, 1 to 4 weeks, or 1 to 3 weeks, or 1 to 2 weeks.

The opacity and/or rigidity of the gel may change over time, as it forms. Thus, for example a semi-solid gel may form initially (e.g. over a period of 1 to 2 days) which gradually becomes more rigid or stiff. Resistance to shear may likewise develop over a period of time. Similarly, the gel may gradually become more clear or more opaque over time. This may be assessed in vivo and in vitro and in vivo degradability may not necessarily be the same as, or parallel in vitro degradability. A fast dissolution in vitro does not necessarily mean a fast dissolution in vivo.

The degradability of the gel may also vary. Thus gels may be obtained which degrade over a period of hours, for example by dissolving when placed in the physiological buffer at room temperature (RT) (i.e. in an in vitro test). Gels may accordingly be obtained which show varying dissolution rates in a physiological agent (e.g. physiological buffer at RT) ranging from 1 or more hours (e.g. at least 1, 2, 3, 4, 5, 6, 7, 8, 9, 10, 12, 15, 18, 20, 22 or 24 hours, or more).

Gels may also be obtained which degrade more quickly, over a period of less than one hour e.g. 30 to 60 minutes. Alternatively, gels may be obtained which do not degrade appreciably (or detectably), or degrade very slowly, for example as manifested by dissolution rates in physiological buffer at RT. Such gels may degrade (e.g. dissolve) over a period of days, for example at least 1, 2, 3, 4, 5, 6, 8, 10, 12, 15, 18, 21, 24, 28 or 30 days, or more.

The gels of the invention are not crystalline (i.e. a solid formed by a repeating pattern of molecules/atoms/ions).

As described in more detail below, the gel composition of the present invention can be formed by simple mixing of an aqueous C-peptide solution with metal ions. Conveniently the metal ions are provided in the form of an aqueous solution, for example an aqueous solution of a metal salt. Thus, the method of gel formation may involve simple mixing of aqueous solutions. Optionally, the C-peptide solution and metal ion solution can be sterilised prior to mixing.

Alternatively, the solutions can be sterilised after mixing. In an alternative embodiment, a C-peptide solution may be prepared and gel formation may be induced by adjusting the pH of the solution, in particular by reducing the pH, for example by adding acid, such as HCl, to the solution. This is also discussed in more detail below.

The term "C-peptide" as used herein includes all forms of C-peptide (which as mentioned above may also be known as proinsulin C-peptide), including native or synthetic peptides and fragments.

Such C-peptides may be the human peptide, or may be from other animal species and genera, preferably mammals. Thus, variants of human C-peptide are included, which may be native variants, or synthetically or artificially derived. C-peptides from a number of different species have been sequenced and are known in the art. It would thus be a routine matter to select a variant being a C-peptide from a species or genus other than human. Several such variants of C-peptide (i.e. representative C-peptides from other species) are shown in FIG. 1 (see SEQ ID NOS. 1 to 24). Thus variants and modifications of native human C-peptide are included as long as they retain C-peptide activity. The C-peptides may be in their native form, i.e. as different variants as they appear in nature in different species or due to geographical variation etc., or may be functionally equivalent variants or derivatives thereof, which may differ in their amino acid sequence, for example by truncation (e.g. from the N- or C-terminus or both) or other amino acid deletions, additions, insertions or substitutions. It is known in the art to modify the sequences of proteins or peptides, whilst retaining their useful activity and this may be achieved using techniques which are standard in the art and widely described in the literature e.g. random or site-directed mutagenesis, cleavage and ligation of nucleic acids etc. Thus the C-peptide may comprise or contain other modifications as compared to a native C-peptide sequence.

Any such modifications, or combinations thereof, may be made, as long as activity is retained. The C-terminal end of the molecule is believed to be important for activity. Preferably, therefore, the C-terminal end of the C-peptide should be preserved in any such C-peptide variants, more preferably the terminal pentapeptide of C-peptide should be preserved. Modifications to the mid-part of the C-peptide sequence (e.g. to residues 13 to 25 of human C-peptide) allow the production of functional variants of C-peptide and are hence covered.

Thus C-peptides may have amino acid sequences which are substantially homologous, or substantially similar to the native C-peptide amino acid sequences, for example to the human C-peptide sequence of SEQ ID NO. 1 or any of the other native C-peptide sequences shown in FIG. 1. Such substantially homologous sequences may include those having at least 30% (or more preferably at least 40, 50, 60, 70, 75, 80, 85, 90, 95, 98 or 99%) similarity to any one of SEQ ID Nos. 1 to 24 as shown in FIG. 1, preferably to the native human sequence of SEQ ID No. 1. Alternatively, the C-peptide may have an amino acid sequence having at least 30% (or more preferably at least 40, 50, 60, 70, 75, 80, 85, 90, 95, 98 or 99%) identity with the amino acid sequence of any one of SEQ ID Nos. 1 to 24 as shown in FIG. 1, preferably with the native human sequence of SEQ ID No. 1. Although any amino acid of C-peptide may be altered as described above, it is preferred that one or more of the glutamic acid residues at positions 3, 11 and 27 of human C-peptide (SEQ ID NO. 1) or corresponding or equivalent positions in C-peptide of other species, are conserved. Preferably all of the glutamic acid residues at positions 3, 11 and 27 (or corresponding Glu residues) of SEQ ID NO. 1 are conserved.

Amino acid sequence identity or similarity may be determined using the BestFit program of the Genetics Computer Group (GCG) Version 10 Software package from the University of Wisconsin. The program uses the local homology algorithm of Smith and Waterman with the default values: Gap creation penalty=8, Gap extension penalty=2, Average match=2.912, Average mismatch=2.003. Thus, functionally equivalent variants of native C-peptide sequences may readily be prepared according to techniques well known in the art, and include peptide sequences having a functional, e.g. a biological, activity of a native C-peptide. Thus a variant of a naturally occurring wild-type or native C-peptide sequence may, for example, differ by 1 to 10, more preferably 1 to 6, or 1 to 4, or 1 to 3 amino acid substitutions, insertions and/or deletions which may be contiguous or non-contiguous as compared to the native or wild-type sequence (e.g. as compared to the sequence of any one of SEQ ID Nos. 1 to 24, preferably SEQ ID No. 1). Representatives of such variants may include those having 1 to 6, or more preferably 1 to 4, 1 to 3 or 1 or 2 amino acid substitutions as compared to SEQ ID No. 1. The substituted amino acid, particularly one of the well known 20 conventional amino acids (Ala (A); Cys(C); Asp (D); Glu(E); Phe(F); Gly(G); His(H); Ile(I); Lys(K); Leu(L); Met(M); Asn(N); Pro(P); Gln(O); Arg(R); Ser(S); Thr(T); Val(V); Trp(W); and Tyr(Y)). Conservative amino acid substitutions are preferred. Thus, an amino acid may be replaced by another which preserves the physicochemical character of the peptide (e.g. D may be replaced by E or vice versa, N by Q, or L; I by V or vice versa). Generally, the substituting amino acid has similar properties e.g. hydrophobicity, hydrophilicity, electronegativity, bulky side chains etc. to the amino acid being replaced. Isomers of the 'native' L-amino acid, e.g. D-amino acids may be incorporated.

Additional alterations may include amino and/or carboxyl terminal fusions as well as intrasequence insertions of single or multiple amino acids. Longer peptides may comprise multiple copies of one or more of the peptide sequences. C and N-terminal protecting groups may be included. As above, a proviso of such variants is that they retain C-peptide activity. Fragments of native or synthetic C-peptide sequences may also have the desirable functional properties of the peptide from which they derive and are hence also included. Mention may be made in particular of the C-peptide fragments described by Wahren et al., in WO98/13384.

Preferred fragments comprise residues 15-31 of native C-peptide, more especially residues 20-31. Peptides comprising the pentapeptide EGSLQ (SEQ ID NO. 25) (residues 27-31 of native human C-peptide) are also preferred. The fragment may thus vary in size from e.g. 4 to 30 amino acids or 5 to 20 residues.

Other preferred fragments include ELGGGPGAG (SEQ ID NO. 26), EGSLQ (SEQ ID NO. 25), ELGG (SEQ ID NO. 27), ELGGGP (SEQ ID NO. 28), GGPGA (SEQ ID NO. 29) or GSLQ (SEQ ID NO. 30). The fragment may also include an N-terminal fragment of C-peptide, typically having the sequence EAEDLQVGAVEL (SEQ ID NO. 31), or a fragment thereof which comprises 2 acidic amino acid residues capable of adopting a conformation where said two acidic amino acid residues are spatially separated by a distance of 9-14 Å between the carbons thereof. Also included are fragments having N and/or C-terminal extensions or flanking sequences. The length of such extended peptides may vary, but typically are not more than 50, 30, 25 or 20 amino acids in length. Chemical modification of the peptide structure is not precluded, e.g. by glycosylation, as long as the structure of the variant remains essentially peptide in nature. All such variants, derivatives or fragments of C-peptide are included, and are subsumed under the term "C-peptide".

The term "C-peptide activity" as used herein means any activity exhibited by a native C-peptide, whether a physiological response exhibited in an in vivo or in vitro test system, or any biological activity or reaction mediated by a native C-peptide, for example in an enzyme assay or in binding to test tissues or membranes.

Thus, it is known that C-peptide increases the intracellular concentration of calcium. An assay for C-peptide activity can thus be by assaying for changes in intracellular calcium concentrations upon addition or administration of the peptide in question. Such an assay is described in for example in Ohtomo et al., (1996), Diabetologia 39, 199-205, Kunt et al., Diabetes 47, A30; Shafqat et al (supra).

Further, C-peptide has been found to induce phosphorylation of the MAP-kinases ERK 1 and 2 of a mouse embryonic fibroblast cell line (Swiss 3T3), and measurement of such phosphorylation and MAPK activation may be used to assess, or assay for C-peptide activity, as described for example by Kitamura et al., (2001), Biochem. J. 355, 123-129.

C-peptide also has a well known effect in stimulating Na+K+ATPase activity and this also may form the basis of an assay for C-peptide activity, for example as described in WO 98/13384 or in Ohtomo et al., (1996), supra or Ohtomo et al., (1998), supra. This is the preferred test to establish C-peptide activity and active variants will preferably induce NA+K+ ATPase activity in the sciatic nerve by at least 50% over basal levels.

An assay for C-peptide activity based on endothelial nitric oxide synthase (eNOS) activity is also described in Kunt et al., supra, using bovine aortic cells and a reporter cell assay.

Binding to particular cells may also be used to assess or assay for C-peptide activity, for example to cell membranes from human renal tubular cells, skin fibroblasts and saphenous vein endothelial cells using fluorescence correlation spectroscopy, as described for example in Rigler et al., supra, Henriksson et al., (2000), Cell Mol. Life. Sci., 57, 337-342 and Pramanik et al., supra. Finally, affinity tests based on measurements of protein binding may be used as activity tests of C-peptide.

Preferably the C-peptide used to form the gel compositions of the invention is in the form of a salt. Thus, the C-peptide to be used in the invention may be presented as a pharmaceutically or physiologically acceptable salt e.g. an acid addition salt. This may include both organic and inorganic salts such as those prepared for example from acids such as hydrochloric, hydrofluoric, sulfuric, sulfonic, tartaric, fumaric, hydrobromic, glycolic, citric, maleic, phosphoric, succinic, acetic, nitric, benzoic, ascorbic, p-toluenesulfonic, benzene-sulfonic, naphthalenesulfonic, propionic, and the like. Preferably, the acid addition salts are those prepared from hydrochloric acid, acetic acid, or succinic acid. Such salts may be prepared by conventional methods well known to those skilled in the art.

Alternatively the C-peptide may be converted into a carboxylic acid salt, such as an ammonium or alkali metal salt e.g. a sodium, potassium or lithium salt etc.

Preferably, however, the C-peptide salts used in the present invention are selected from sulphates, chlorides, acetates, phosphates, citrates, formates or nitrates. Conveniently, a C-peptide acetate salt may be used.

To form the gel, a C-peptide solution may be prepared. An aqueous solution of the C-peptide (e.g. C-peptide salt) is preferably used. For example, an aqueous solution of C-peptide (preferably of a C-peptide salt such as acetate) can be prepared by adding the C-peptide to water. However, pH may be important in preparing C-peptide solutions. Native human C-peptide has low pI (pI 3.45) and consequently an acidic pH-shift occurs when it is dissolved. It may be necessary to add alkali (neutralise) the solution in order for the C-peptide to dissolve. To prepare a concentrated C-peptide solution (e.g. at 10 mg/ml or more e.g. 30 mg/ml) addition of alkali (e.g. NaOH or other base) is generally found to be necessary, as C-peptide will not dissolve at low pH. This is described in the Examples below. Solutions of C-peptide in water are preferred, but any aqueous solutions (e.g. in weak buffers) could be used.

As mentioned above, the gel compositions of the present invention may be formed by adjustment of pH of the composition and/or addition of divalent metal ions. Thus, to form a gel, a C-peptide solution may be prepared. A gel may then be induced or caused to form, (or the gel-forming process may be started) by altering or adjusting the pH of the solution by adding alkali or acid, (base or acid equivalents) preferably in the form of an acid or alkali solution, and/or by adding divalent metal ions to the C-peptide solution. An appropriate solution may be an aqueous solution of NaOH, KOH or LiOH, and HCl, respectively, in a concentration range of 0.5-2 M.

Gels formed by adding divalent metal ions represent a preferred aspect of the present invention.

Thus, in one embodiment, the present invention provides a pharmaceutical composition in the form of a gel comprising C-peptide and divalent metal ions, wherein said metal ions are the sole gel-forming agent in the composition.

Such a gel composition may be used for the sustained released of C-peptide. As mentioned above, such a gel composition may be formed by adding divalent metal ions to a C-peptide solution (preferably a solution of a C-peptide salt, e.g. C-peptide acetate).

The metal ions may conveniently be added in the form of a solution of metal ions. An aqueous solution providing metal ions may thus be prepared.

The metal ions may be provided in the form of a metal salt. Thus, a solution of a divalent metal salt may be provided for use according to the present invention. Such a solution is generally an aqueous solution. A metal salt solution may conveniently be prepared by dissolving a water-soluble metal salt in water.

The metal ion may be any divalent metal ion. For example the metal may be selected from zinc(II), nickel(II), cobalt(II), magnesium, calcium, manganese, iron(II) or copper(II). Preferably the metal is zinc or calcium. Most preferably the metal is zinc.

The divalent metal may be used in the form of a desired or convenient salt. Generally, a water-soluble salt will be used. Suitable salts may be selected from sulphates, phosphates, citrates, chlorides, acetates, formates or nitrates. Preferably the salt to be used is a chloride and more preferably the metal salt is zinc chloride or calcium chloride. Zinc chloride is preferred.

Combinations of metal ions or metal salts can also be used to form the gel of the present invention, for example different salts of one metal or different metals of different salts or different metals of the same salt (i.e. the same counter-ion). Thus, for example zinc chloride and zinc sulphate or zinc chloride and calcium sulphate or zinc chloride and calcium chloride could be used.

Further, different combinations of different salts of C-peptide can be used to form the gel. For example, both C-peptide acetate and C-peptide sulphate can be used in conjunction with a metal salt or combination of metal salts. Different "C-peptides" i.e. different variants, fragments and derivatives can also be used together to from the gel of the present invention. For example, native human C-peptide and the C-terminal pentapeptide of native human C-peptide can be used.

To prepare the gel, the C-peptide solution and the metal ion solution are brought into contact. Thus, the metal ion solution may simply be added to the C-peptide solution, or vice versa. The two solutions may be mixed and left, or allowed to stand, until gel formation occurs. The terms "mix" and "mixed" etc. are thus used herein to include any manner of bringing the respective reagents (i.e. solutions) into contact. One solution may be added to another and they may be mixed, for example by stirring or shaking, e.g. on a vortex mixer.

The metal ions as used in the present invention allow the formation of a gel when mixed with C-peptide. In this regard, the metal ions are the sole gelling agents used to form the gel, or present in the gel. Therefore the use only of the metal ions allows the formation of the gel and additional gelling agents, for example as known in the art, are not used to form the gel of the present application. Particularly excluded is use of phenolic and/or alcoholic aromatic compounds as gel-forming agents.

The C-peptide/metal ion mixture may be left for any period of time suitable or required for a gel to form. The mixture of C-peptide and metal ions is preferably left for at least 12 hours for gel formation to occur. More preferably, the mixture of C-peptide and metal ions is left for at least 24 hours, 36 hours, 48 hours, 60 hours, 72 hours, 84 hours or 96 hours or 5, 6, 7, 8, 9, 10, 11, 12, 13, 14, 15, 16, 17, 18, 19, 20, 21, 22, 23, 24 or 25 days. In certain embodiments the mixture is left for at least one, two or three days, e.g. for 1, 2, 3 or 4 days, or 1 to 6 days, 1 to 4 days, or 1 to 3 days. In other cases, longer periods of time are required, e.g. 1 to 15, 1 to 12, 1 to 10 or 1 to 9 days, e.g. up to 9, 10, 11 or 12 days or more, up to 20, 21, 24, 27, 30 or 35 days or more. It will be appreciated however by a person skilled in the art that the gel formation time may be altered by appropriate selection of conditions, or concentration of reagents or by the addition of other components to the mixture.

The gel formation of the present invention can occur at any temperature. However, preferably the C-peptide and metal salt mixture is incubated between 1 and 40° C. or 1-25° C., more preferably between 1-20° C. In some embodiments, the mixture may be incubated between 2-8° C. for gel formation. Room temperature is preferred.

In other embodiments, temperatures of 15-40° C. e.g. 15-25° C. or 37° C. or 40° C. may be used. Conveniently the mixtures may be left to stand at room temperature.

The pH of the compositions may influence the optimum temperature for gel formation and this may be investigated by simple and routine experiments, and an appropriate temperature selected depending upon the precise conditions, reagents and concentrations selected.

The pH of the compositions may vary depending upon the reagents selected, concentrations used etc. Generally speaking the pH may lie in the range 4 to 7. A preferred pH range is 4.5 to 6, more preferably 4.5 to 5.5.

As noted above, the addition of a base (e.g. NaOH) may be necessary to prepare a C-peptide solution and solubility of C-peptide is dependent upon pH. Thus, C-peptide solutions of varying pH may be prepared, depending upon the concentration of C-peptide and/or amount of base added etc. As shown in the Examples below, C-peptide solutions of selected or pre-determined pH may be prepared by appropriate addition of required amounts of base- and/or acid equivalents, (by calculating "base excess" with reference to a titration curve of C-peptide as a function of the added number of equivalents of NaOH per unit volume, referred to as "base excess").

C-peptide solutions of pH 5.1 ∀ 0.1 or above may be made, for example pH 5.2 up to pH 9.0. It is generally preferred to use C-peptide solutions of pH 5.2 to 6.0. The starting pH of the C-peptide solution may be used to help determine the final pH of the mixture (although a pH change will occur upon addition of the metal ions). Experiments may be conducted to determine an appropriate pH, and how it may be achieved by using of different reagents of different concentrations, volumes and starting pH etc.

The final pH of the C-peptide/metal ion mixture may also be adjusted as desired, by appropriate addition of acid or base. The pH of the final mixture may lie in the region of pH 5-6.

Different concentrations of the metal salt and C-peptide can be used to form the gel. The concentration of metal salt may vary depending upon the metal salt used. For example, in the case of zinc chloride, this may be used at concentrations of between 1-300 mg/ml, e.g. 1-200 mg/ml. Different concentrations or concentration ranges may be used according to choice e.g. 1-50 mg/ml or between 1-30 mg/ml, 1-25 mg/ml or 1-20 mg/ml. Suitable ranges include 5-30, 5-25, 6-30 or 6-25 mg/ml. Other ranges may be 50-200 mg/ml, or 100-200 mg/ml. Appropriate metal ion concentrations may lie in the range of 0.001 M to 0.5 M, preferably 0.005 M to 0.3 M or 0.01 M to 0.2 M.

C-peptide may be used at concentrations of between 1-70 mg/ml, preferably between 10-50 mg/ml. More preferably C-peptide is used at concentrations of at least 10, 15, 20, 25, 30, 35 or 40 mg/ml. Most preferably C-peptide is used at concentrations of at least 20 or 25 mg/ml, e.g. 20-30 mg/ml (e.g. at 20, 25 or 30 mg/ml).

Alternatively viewed, different molar ratios of metal ion: C-peptide can be used for gel formation. Generally speaking, these may range widely from e.g. 0.5 to 70. Different molar ratios may result in different gel characteristic and release rates. It has generally been found that lower molar ratios may result in more rapid release, and higher ratios in slower release. The molar ratio of metal:C-peptide used can affect the rate of release of the metal ions and/or peptide from the gel and hence the molar ratio selected to be used may depend upon how quickly the C-peptide is intended to be released, for example to a particular patient. Preferably, the gel allows sustained release of C-peptide over a period of time. Hence, a lower molar ratio of metal salt:C-peptide may result in a gel where the rate of release of the metal and C-peptide is faster, although the initial release rate is slower. A high molar ratio of metal salt:C-peptide may result in a gel where release of the metal ions and peptide occurs over a longer period of time, although the initial release may be faster. Representative molar ratios may lie in the range 5-30, 8-30, 10-30 or 20-30, for example where more rapid release is required (e.g. in the case of a preparation intended for once- or twice-daily administration). Alternatively, higher ratios may be selected, for example in the range 30-60 or 40-60, for example where slower release is desired (e.g. in the case of once or twice-weekly administration).

Release rates of the C-peptide from the gel will, as mentioned above, be dependent on a number of factors, including molar ratios and concentrations of the metal salt and C-peptide used, pH of the composition, how exactly the gel was formed etc.

Rates of release are discussed generally above. For example, between 0.1-10% of C-peptide in the gel may be released per hour. More preferably, 0.2, 0.3, 0.5, 0.8, 1, 2, 3, 4, 5, 6, 7% of the C-peptide may be released per hour.

Gels may be prepared from which it will take between 8 hours and 4 weeks or more for at least 80, 90 or 100% of the C-peptide to be released. In certain embodiments it may take between 8 hours and 7 days e.g. 8 hours and 5 days, or 12-96 hours or 20-72 hours or 24-48 hours. In other embodiments longer release may be obtained. For example, it may take 2 days to 4, 3, 2 or 1 week, e.g. 3-21 days, 3-18 days, 4-15 days, 4-12 days, etc.

However, it would be appreciated by a person skilled in the art that the release rates described above may vary depending on various factors.

The above release rates from the gel can be determined by transferring an amount (e.g. 5 g) of the gel formed (e.g. after a 3-10 day incubation) to a pre-soaked dialysis membrane tubing. The filled tubing is then sealed using plastic clamps and placed in a beaker with 100 ml warm (37°+/−1° C.) 0.9% aqueous sodium chloride solution (the release medium) with slow magnetic stirring. Aliquots of approximately 1 g of release medium are withdrawn at selected time points and the samples assayed for metal ion content using an atomic absorption spectrometer or for C-peptide content (e.g. by ELISA). A reference mixture consisting of water and 20% (w/w) metal salt solution can be used to normalise any results obtained.

In another embodiment the present invention provides a composition comprising C-peptide and metal ions obtainable by mixing an aqueous solution of C-peptide with an aqueous solution of a metal salt and leaving said mixture for a length of time sufficient to form a gel.

Generally speaking the C-peptide solution will be a solution of C-peptide salt.

A further embodiment of the present invention provides a method of producing a composition in gel form comprising C-peptide, said method comprising the steps of (i) mixing an aqueous solution of C-peptide with an aqueous solution of a metal salt and (ii) leaving the mixture for a length of time sufficient to form a gel.

Details of various aspects of these embodiments of the invention are discussed above. In particular, as discussed above, the pH of the C-peptide solution may be adjusted or pre-determined. Thus such a method may include the step of preparing an aqueous C-peptide solution of pre-determined (or desired or selected) pH or of adjusting the pH of an aqueous C-peptide solution. pH may also be adjusted after mixing of the two solutions. Thus the pH of the mixture may be adjusted.

It will be seen from the above discussion, that pH may play a role in the gel formation process using C-peptide and metal ions. It has further been shown that gels may be formed from aqueous solutions of C-peptide alone, simply by adjusting the pH of the solution. In particular, reducing the pH of an aqueous C-peptide solution may cause a gel to form. Such a gel may retard the release of C-peptide from the composition, and may thus be used as the basis of a sustained release pharmaceutical composition.

Thus, a further method for forming a C-peptide-containing composition in gel form may involve simply adjusting the pH of an aqueous C-peptide solution and allowing a gel to form. Such adjustment will generally be reducing the pH of the solution. A gel may be allowed to form by leaving the reduced-pH solution for a length of time sufficient for a gel to form (e.g. allowing it to stand). The pH adjustment may be carried out using well known methods. Thus pH may be reduced by adding acid (e.g. an acid solution such as HCl) to an aqueous C-peptide solution.

An aqueous C-peptide solution may be prepared as discussed above. The pH of the solution may be determined after it is made. Alternatively, a C-peptide solution of pre-determined pH may be made. Thus, as discussed above, a titration curve may be prepared as a function of the added number of equivalents of NaOH per volume unit (referred to as "base excess"). Once the titration curve of a C-peptide is known, the pH of a solution may be predicted (pre-determined) simply by calculating the base excess and adding the appropriate amounts of either base or acid-equivalents (e.g. NaOH- or HCl-equivalent) to the C-peptide solution.

The pH of a C-peptide solution of known pH may be reduced to a desired or pre-selected level by adding appropriate amounts of acid-equivalents (e.g. HCl-equivalents) to the solution.

The pH of a C-peptide solution may be reduced to pH 5.0 or below for a gel to form. An appropriate pH range to which pH may be reduced may lie in pH 1 to 5, e.g. 1 to 4.9, 4.99 or 4.98, or 1.2 to 4.99, 4.98 or 4.95 or 1.5 to 4.95, more particularly 1.8, 1.9, 2.0, 2.2, 2.5, 2.7, 3.0, 3.2, 3.5, 3.8, 3.9 or 4.0 to 4.99, 4.98, 4.97, 4.96 or 4.95, e.g. 4.0 to 4.99 or 4.0 to 4.98 etc.

Gel formation by reducing pH may start to take place within hours e.g. within 1 to 5, e.g. 2 to 4 e.g. 3 hours. If left for longer periods e.g. for 12, 18 or 24 hours, stiffer gels may start to form. Thus, the reduced pH solution may be left for at least 12 or 24 hours or 1, 2, 3, 4 or 5 days or more for a gel to form.

Such "pH-based" gels may conveniently be formed at room temperature, but other temperatures may be used e.g. up to 40° C. (e.g. 37° C.). However, temperatures around room temperature are preferred e.g. 15-25° C., e.g. 18-22° C.

C-peptide concentrations may be as discussed above in relation to the metal ion-based gels. Generally speaking C-peptide concentrations of at least 10 mg/ml, or at least 15, 20, 25 or 30 mg/ml are preferred. A suitable C-peptide concentration range may lie in 10-35, e.g. 10-30 mg/ml.

It has generally been found that pH-based gels may release C-peptide more quickly. Thus, such gels may be used to prepare sustained-release compositions which release C-peptide over a period of up to 24 hours e.g. 8 to 24 hours or 8-12 hours.

The gels of the present invention may comprise other components in addition to the C-peptide (and metal ions if present).

Such components include viscosity-adjusting agents (preferably non-ionic) and co-solvents which are miscible with water, e.g. glycerol, propylene glycol and PEG 400.

The gels of the present invention may also comprise tonicity-modifying agents, such as sodium chloride, potassium chloride, glycerol, glucose, dextrose, sucrose, mannitol, etc.

The gels of the inventions may also comprise optional components, such as buffering agents, preservatives, antioxidants, chelating agents, flavouring and taste-masking agents. However, their identity and the amounts employed should be at a minimum in order not to have a detrimental effect on gel stability. For a given component this can be ascertained by simple experiments, which are routine and well within the understanding of the skilled person.

The gels of the present invention can also comprise further pharmaceutically-active agents (e.g. other peptides/proteins) in addition to the C-peptide. In a preferred embodiment, the gels may also comprise further active agents which can be used to treat diabetes and/or its complications, for example insulin.

The gels of the invention have a utility in C-peptide based therapies, that is in the therapy of (i.e. in combating) any condition which may be alleviated or improved by, or which responds to, C-peptide administration. "Therapy" and "combating" in this regard include both treatment and prophylaxis. In particular the gels of the invention can be used for the therapy of (i.e. for combating) diabetes and diabetic complications, most notably type 1 diabetes and its complications. As used herein the term "diabetic complications" includes all complications which may be associated with various forms of diabetes, in particular retinopathy, neuropathy and nephropathy. The gels may thus be used in treatment of type 1 diabetes patients with one or more of the above-mentioned complications, or for preventing or retarding the development of such complications. The treatment of Type 2 diabetes patients is not excluded. Thus, the gels may be used in C-peptide replacement therapy of diabetic patients.

A further aspect of this invention thus provides a composition of the invention as hereinbefore defined, for use in therapy, and in particular in C-peptide therapy, (e.g. C-peptide replacement therapy in diabetes), and also the use of such a composition in preparing a medicament for use in C-peptide therapy (e.g. for combating diabetes or diabetic complications).

Alternatively viewed, the present invention provides a method of combating diabetes or diabetic complications in a patient, said method comprising administering to said patient a composition of the invention as hereinbefore defined.

Pharmaceutical compositions comprising more than one gel composition of the invention are also contemplated. For example, pharmaceutical compositions comprising different gel compositions of the present invention are covered. However, the respective gels used in such combinations need not both be included in the same composition/medicament and could be administered separately in separate compositions/medicaments simultaneously or sequentially.

A further aspect of the invention thus provides a product containing two or more gel compositions of the present invention as a combined preparation for simultaneous, separate or sequential use in C-peptide based therapy (e.g. in combating diabetes and/or diabetic complications).

The gel composition may also be used in combination or conjunction with other agents active or effective to treat diabetes and/or its complications. Such other active agents include for example insulin. In such "combination" therapies the gel composition(s) and second active agent may be administered together in the same composition or separately in separate compositions, simultaneously or sequentially.

A further aspect of the invention thus provides a product containing a gel composition of the invention as hereinbefore defined, together with a further active agent effective to combat diabetes or diabetic complications, as a combined preparation for simultaneous, separate or sequential use in combating diabetes and/or diabetic complications.

Preferably such a further active agent is insulin.

In such combined therapies, where insulin is used, it is to be understood that the term "insulin" encompasses all forms, types and derivatives of insulin which may be used for therapy e.g. synthetic, modified, or truncated variants of the active human insulin sequence.

The gel formulations and/or compositions of the invention may be administered in any convenient way, e.g. orally or parenterally, for example by the subcutaneous or intramuscular route or by implantation. Preferably the gel formulations of the present invention are administered by subcutaneous injection. The gel formulations are further preferably injected once the gel formation is complete. Hence, in one embodiment the solutions of C-peptide and metal salt can be mixed and left to form the gel in the container e.g. syringe used for administration. Alternatively, the gel formulation can be transferred to the container e.g. syringe after its formation. The gel compositions or products of this invention may also comprise a pharmaceutically acceptable carrier and optionally, other therapeutic ingredients, for example human insulin. The total amount of active ingredients in the gel formulation and/or composition may vary from 99.99 to 0.01 percent of weight. The carrier must be acceptable in the sense that it is compatible with other components of the composition and is not deleterious to the recipient thereof. The gel compositions of the present invention can be administered several times a day, for example between 1-5 times a day. However, preferably, the gel formulations and/or compositions are administered between once or twice a day and once every ten days, for example once every two or three days, or once a week.

The amount of gel which is administered can be between 0.1-2 ml, for example 0.1, 0.2, 0.3, 0.4, 0.5, 0.6, 0.8, 1.0, 1.2, 1.4, 1.6 or 1.8 ml, e.g. 0.1-1 ml, or 0.1-0.5 ml e.g. 0.2-0.5 ml.

The compositions of the invention may be formulated according to techniques and procedures well known in the art and widely described in the literature, and may comprise any of the known carriers, diluents or excipients.

BRIEF DESCRIPTION OF THE DRAWINGS

The invention will now be described in more detail in the following non-limiting Examples and with reference to the drawings in which:

FIG. 1 is an alignment showing C-peptide amino acid sequences from different species;

EXAMPLE 1

C-Peptide-Zinc Ion Complexes

Figure 2:
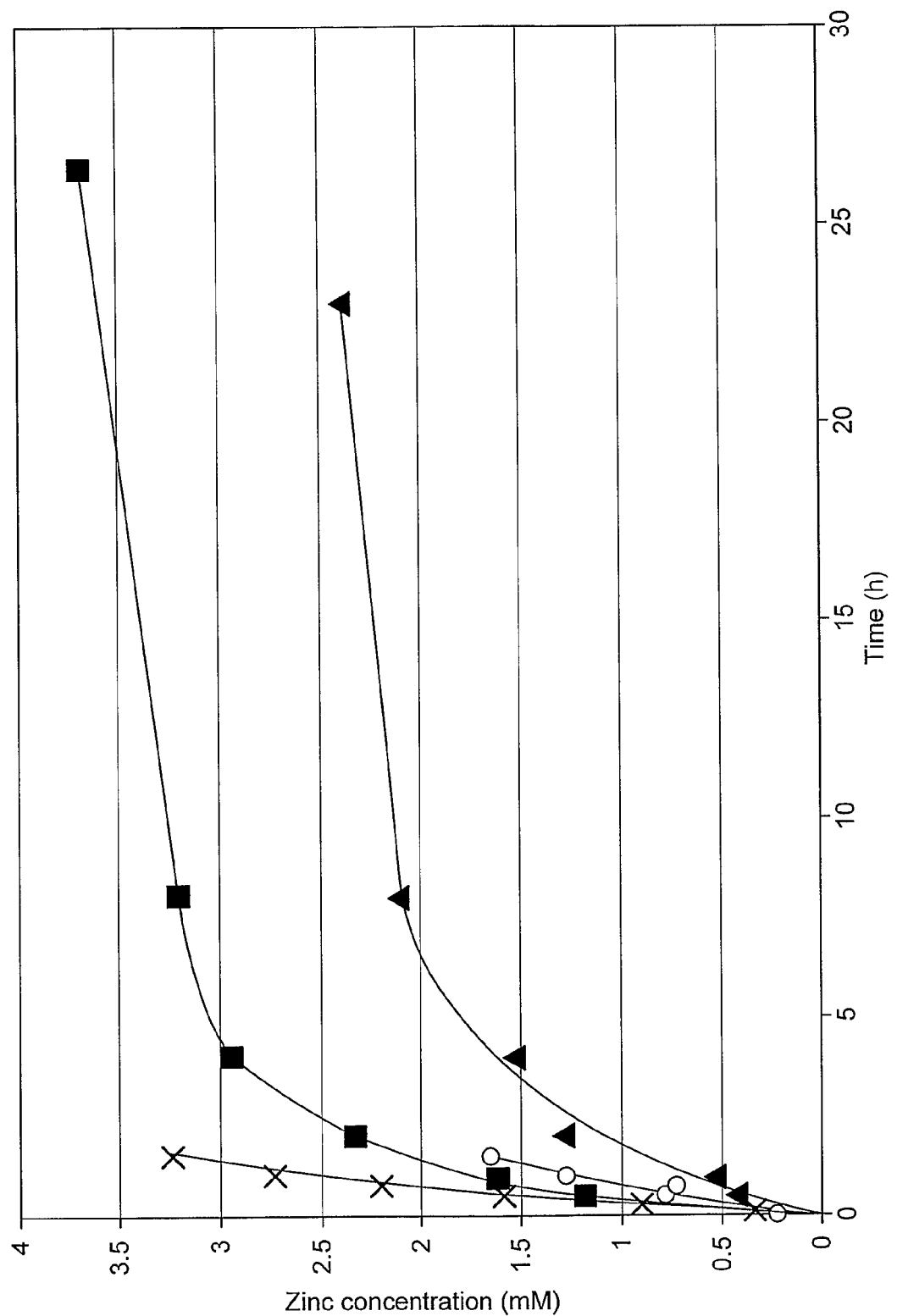
FIG. 2 shows the release of zinc ions from the C-peptide gel formulation at two molar ratios of zinc:C-peptide (▲: low molar ratio zinc:C-peptide (5.09); ■: high molar ratio zinc: C-peptide (9.85); ○: reference solution for low molar ratio; x: reference solution for high molar ratio).

C-peptide solutions, approximately 20 mg/g and 30 mg/g, were prepared in the following way. C-peptide, as acetate salt, from Schwarz Pharma AG, Germany, was suspended in membrane-filtered water using a magnetic stirrer. The pH was then adjusted to 5-6 by drop-wise addition of 10% NaOH (aq.) during stirring at room temperature. A clear solution was obtained after 1 h.

Calcium and zinc chloride solutions were prepared by dissolving the corresponding salts in membrane-filtered water.

A number of samples of C-peptide and calcium or zinc chloride mixtures in aqueous solution were prepared in glass tubes using a micropipette. The mixtures were thoroughly shaken on a vortex mixer and then allowed to stand at room temperature for at least two days. The appearances of the samples were noted after two days and three weeks and the results are presented in Table 1 and 2.

TABLE 1

Samples based on 20.5 mg/g C-peptide solution

| | Sample no. | | | |
|---|---|---|---|---|
| | 1 | 2 | 3 | 4 |
| C-peptide, 20.5 mg/g | 375 µl | 375 µl | 375 µl | 375 µl |
| $ZnCl_2$, 100 mg/g | 25 µl | | | |
| $ZnCl_2$, 200 mg/g | | 25 µl | | |
| $CaCl_2 \cdot 2H_2O$, 100 mg/g | | | 25 µl | |
| $CaCl_2 \cdot 2H_2O$, 200 mg/g | | | | 25 µl |
| Amount C-peptide/ml | 19.2 mg | 19.2 mg | 19.2 mg | 19.2 mg |
| Amount added salt/ml | 6.3 mg | 12.5 mg | 6.3 mg | 12.5 mg |
| Molar ratio $Me^{2+}$/peptide | 7.2 | 14.4 | 6.7 | 13.4 |
| Appearance after 2 days at room temperature | cloudy solution + gellous particles | cloudy solution + gellous particles | slightly cloudy solution | slightly cloudy solution |
| Appearance after 3 weeks at room temperature | clear & gellous | clear & gellous | slightly cloudy solution | slightly cloudy solution |

TABLE 2

Samples based on 30.6 mg/g C-peptide solution

| | Sample no. | | | |
|---|---|---|---|---|
| | 5 | 6 | 7 | 8 |
| C-peptide, 30.6 mg/g | 375 µl | 375 µl | 375 µl | 375 µl |
| $ZnCl_2$, 100 mg/g | 25 µl | | | |
| $ZnCl_2$, 200 mg/g | | 25 µl | | |
| $CaCl_2 \cdot 2H_2O$, 100 mg/g | | | 25 µl | |
| $CaCl_2 \cdot 2H_2O$, 200 mg/g | | | | 25 µl |
| Amount C-peptide/ml | 28.7 mg | 28.7 mg | 28.7 mg | 28.7 mg |
| Amount added salt/ml | 6.3 mg | 12.5 mg | 6.3 mg | 12.5 mg |
| Molar ratio $Me^{2+}$/peptide | 4.8 | 9.7 | 4.5 | 9.0 |
| Appearance after 2 days at room temperature | opaque & gellous, releasing water upon shaking | opaque & gellous, releasing water upon shaking | opaque & gellous, releasing water upon shaking | opaque & gellous, releasing water upon shaking |
| Appearance after 3 weeks at room temperature | opaque & gellous | opaque & gellous | opaque & gellous | opaque & gellous |

Addition of the divalent metal cations $Zn^{2+}$ and $Ca^{2+}$ to a relatively diluted C-peptide solution leads to complex formation and a subsequent formation of a gellous precipitate, which eventually leads to the formation of a macroscopic structure with gel-like appearance and properties.

From comparison of the results in Tables 1 and 2, it is evident that the highest viscosity was obtained for samples containing the highest C-peptide concentration (Table 2). A comparison of the tendency of releasing water upon gentle shaking, i.e. syneresis, between samples no. 5 and 6 (Table 2), where the latter sample released the least amount, reveals that a more concentrated $ZnCl_2$ solution favoured a stronger gel formation. The $ZnCl_2$ solution was more favourable to use than the $CaCl_2$ solution in admixture with the C-peptide solution, since samples no. 5 and 6 have a more opaque appearance than samples no. 7 and 8 (Table 2). An opaque appearance indicates the presence of a large number of microscopic aggregates and thus a high degree of gel formation. Samples no. 5 and 6 were also more viscous than samples no 7 and 8, again indicating a higher degree of gel formation.

From these experiments it can be concluded that gel formation according to the present invention is favoured by a high C-peptide concentration in combination with a high metal ion concentration, where $Zn^{2+}$ ions are more efficient than $Ca^{2+}$ ions to form gels.

EXAMPLE 2

In Vitro Release of Zinc Ions from Samples Comprising C-Peptide Gels

In order to assess the effect of the molar ratio of C-peptide polyanion to zinc ions on in vitro release characteristics of the gels, the following tests were performed.

A solution of C-peptide acetate, 30.0 mg/g, was prepared as described in Example 1. Predetermined amounts of this solution and 20% (w/w) aqueous zinc chloride solution were transferred to a plastic syringe. The syringe was sealed with a plastic cap, its contents carefully mixed and then refrigerated for at least 3 days to ensure complete gel formation. The gel, approximately 5 g, was then transferred to a pre-soaked dialysis membrane tubing (Spectra/Por 3 regenerated cellulose, molecular weight cut off 3500 Da, length 17 cm, flat width 4.5 cm; Spectrum Laboratories Inc., CA). The filled tubing was sealed using plastic clamps and then placed in a glass beaker with 100 ml warm (37° C.±1° C.) 0.9% aqueous sodium chloride solution as the release medium with slow magnetic stirring, 70 rpm. Aliquots of about 1.0 g of release medium were withdrawn at selected time points, without compensating for the loss in volume. Samples were assayed for zinc content using a Varian SpectrAA 220 atomic absorption spectrometer (wavelength 213.9 nm; standard curve: 6.12-30.6 µM $Zn^{2+}$; triplicate measurements on each sample). A reference mixture without C-peptide, consisting of pure water and 20.0% (w/w) aqueous zinc chloride solution was mixed, treated and analysed in the same way as the C-peptide mixtures (except refrigeration after mixing). Release curves were plotted with normalised molar theoretical cumulative zinc ion concentration versus time, and the results are shown in FIGS. 2 and 3.

Figure 3:
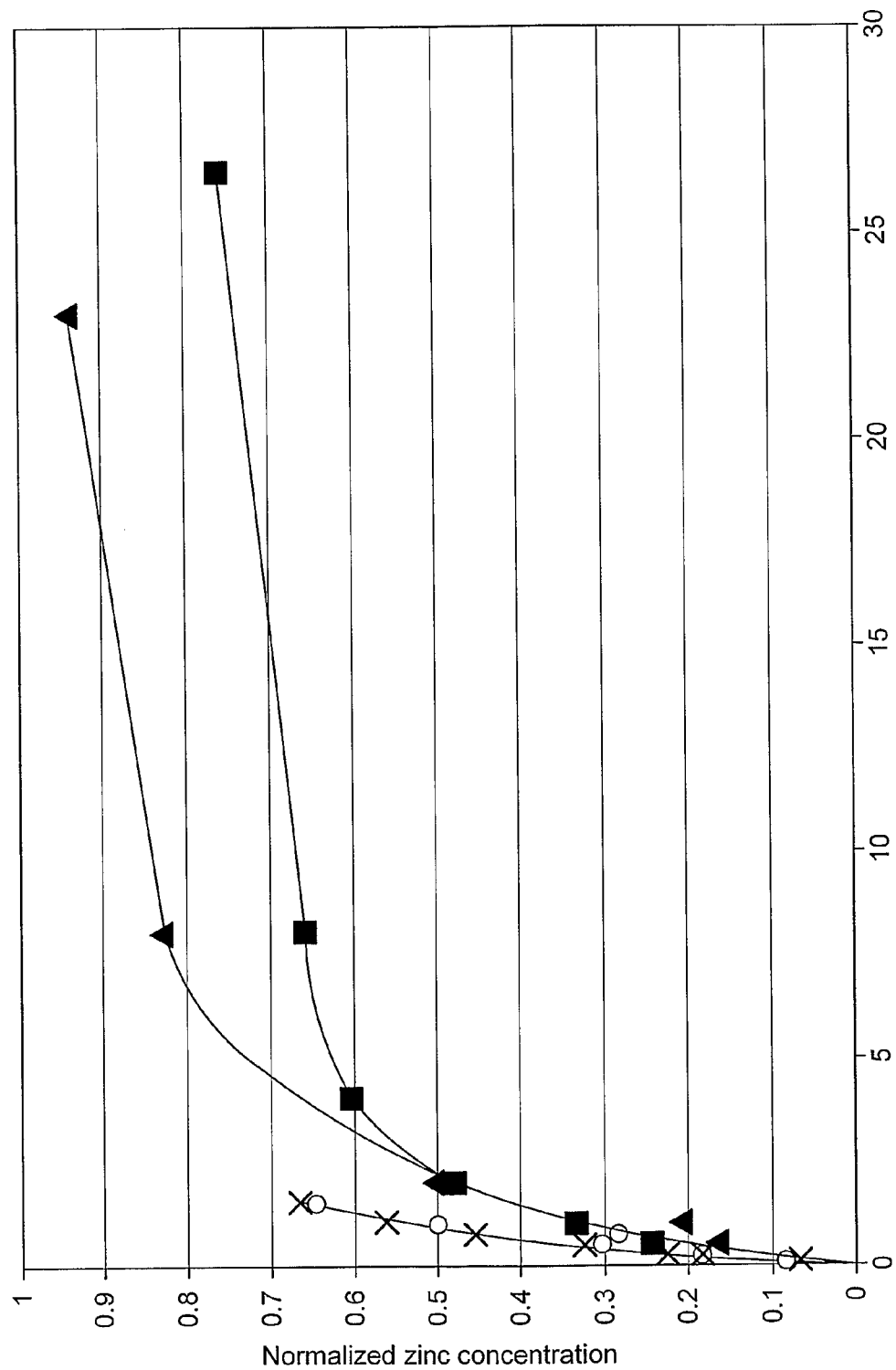
FIG. 3 shows the release of zinc ions (normalized concentrations) from a C-peptide gel formulation at two molar ratio of zinc:C-peptide (▲: low molar ratio zinc:C-peptide (5.09); ■: high molar ratio zinc:C-peptide (9.85); ○: reference solution for low molar ratio; x: reference solution for high molar ratio).

It is evident from the release curves in FIGS. 2 and 3 that the presence of C-peptide delayed the release of zinc ions from the formed gels through the dialysis tubing. Without C-peptide half the equilibrium concentration of zinc ions in the release medium in both cases was attained within 1 h (FIG. 3), with an expected, somewhat faster release from the system with the highest initial zinc concentration (FIG. 2).

In contrast, the gel formation of zinc ions with C-peptide affects the release profile in a manner dependent on the composition, i.e. the ratio of peptide to zinc. For a molar ratio of 5.09, i.e. 5.09 moles of $Zn^{2+}$ to 1.00 mole C-peptide, half the equilibrium concentration was reached after about 2 h (FIG. 3). A higher molar ratio, 9.85 moles of $Zn^{2+}$ to 1.00 mole C-peptide, also gave half the equilibrium concentration after about 2 h (FIG. 3), but resulted in a slightly faster initial release rate (FIG. 2). A possible explanation of this is that the gel is "saturated" with zinc ions—the system consists of two fractions of zinc, one fraction of "free" zinc ions, which give rise to an initial fast release, and another fraction "bound" to C-peptide, which give rise to a slower release (vide infra).

Also the time to attain complete release of zinc was affected by the composition of the gel. At a molar ratio of 5.09 moles of zinc per mole C-peptide, 70% of the zinc was released from the gel at about 5 h, whereas at the higher molar ratio, 9.85 moles of zinc per mole C-peptide, the corresponding cumulative amount of zinc was released at 15 h. For the former composition, 80% of the zinc was released after 8 h, whereas for the latter composition a release of 80% was not attained, at least not at 26 h (FIG. 3). This is mainly the result of a much stronger gel formation between C-peptide and zinc when the number of zinc ions is increased. However, different experimental settings (smaller volume of sample in dialysis tubing, smaller volume of release medium, faster stirring rate, etc.) would indeed lead to a different release profile and eventually to a 100% release of zinc, but the comparison between different compositions at arbitrary but consistent conditions is still valid.

It is anticipated that further lowering of the molar ratio could lead to even slower initial release rate. However, there should exist an optimal molar ratio of zinc and C-peptide, for a given C-peptide concentration, where the interactions between the metal cations and the anionic peptide favours gel formation. The curves show that the release of zinc ions from the complexes is more or less sustained due to the interactions of theses ions with C-peptide: the highest molar ratio of zinc to C-peptide investigated was more effective in reducing the release rate than that of the lower molar ratio.

EXAMPLE 3

Preparation of C-Peptide Solutions

Materials and Methods
C-Peptide
Recombinant human C-peptide prepared by Schwarz Pharma AG, Germany was used.
All other chemicals used were of analytical grade.
Methods
All experiments were carried out in an aqueous environment and at room temperature (RT), unless stated otherwise.
Standard Preparation of a Homogeneous C-Peptide Solution:
  weigh the desired amount of C-peptide and bring it over quantitatively into an erlenmeyer flask
  add approximately 60% of the water for injection (WFI); note the amount
  gently swirl the flask and wait until most of the C-peptide has dropped into the liquid phase. Beware that the C-peptide does not attach to the wall above the liquid
  add small amounts of 0.25 M NaOH and gently swirl the flask for some time. Allow the C-peptide to dissolve; the dissolving process proceeds slowly. Repeat this step until all C-peptide has dissolved; note the amounts
  make up to the total volume with WFI
Experiments, Results and Discussion
Preparation of C-Peptide Solutions It was necessary to prepare a homogeneous C-peptide solution before any formulation could be prepared. The pH of the solution played an important role in the dissolving process.

The C-peptide concentration tested in this study was 30 mg/mL. Basically, for preparation of the formulations a relatively small amount (20-100 µL) of cation solution was added to a solution (750 µL) of 30 mg C-peptide/mL, through which the end concentration of the C-peptide in the formulation was 26.5-29.2 mg/mL. However, it appeared that the C-peptide solution could not simply be prepared by dissolving the required amount of C-peptide in WFI. The C-peptide molecule contains more acidic side groups than basic side groups, which results in a low pI (pI≈3.0) and, consequently, a decrease of the pH when it gets dissolved; an acidic pH-shift occurs and the C-peptide does not dissolve at low pH. Another dissolution method had to be found.

The easiest way to getting a clear solution of C-peptide appeared to be suspending the C-peptide in water and slowly adding a NaOH solution until the C-peptide has completely dissolved. However, it was difficult to follow this procedure when small amounts (≤5 mL) were prepared; the pH of the obtained solutions quickly became too high (pH≥8). Accordingly, the procedure indicated in the methods was derived.

It appeared that the solution did not become clear but stayed slightly turbid. Even when a larger amount of NaOH was added and the pH rose from 5 till 8, the solution did not become clear.

In practise, it was necessary to prepare amounts of the C-peptide solution larger than 10 mL because otherwise the pH of the solution quickly became too high, even after adding small amounts of the base.

Figure 4:
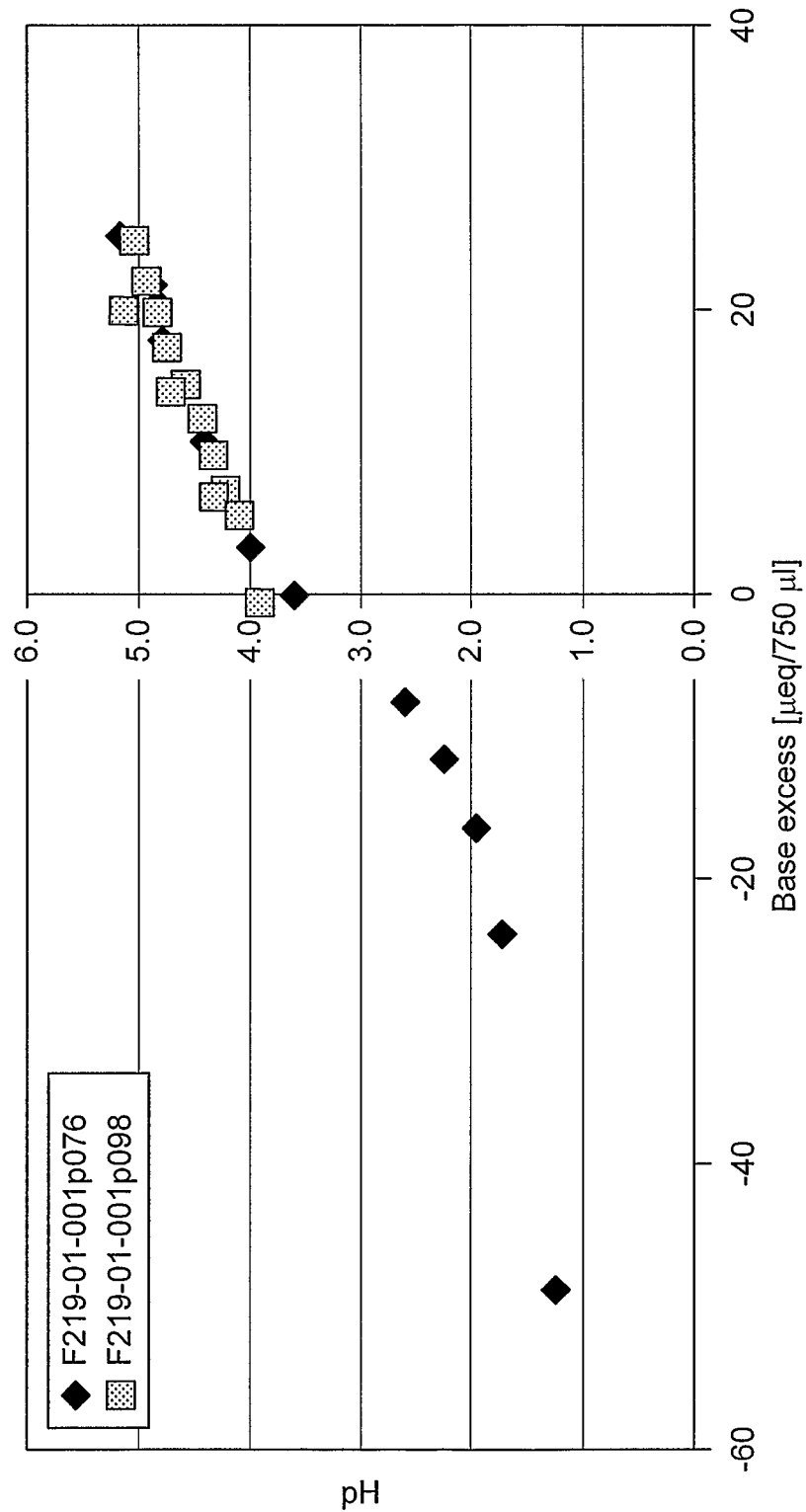
FIG. 4 is a graph showing pH as a function of the Base Excess in C-peptide formulations. The two formulations were prepared on two different days and according to the same procedure. ♦F219-01-001p076, □F219-01-001p098.

Further experiments showed that a homogeneous 30 mg/mL C-peptide solution could be prepared when the end-pH of the solution was higher than pH 5.1-5.3. Nevertheless, the solution stayed slightly turbid, also at much higher pH (pH 8-9). At lower pH the C-peptide precipitated.
Prediction of the pH of the C-Peptide Solutions by Calculation of the Base Excess
  Through the dissolving method, as stated under "Materials and methods" above, it was possible to calculate and prepare a titration curve of C-peptide as a function of the added number of equivalents of NaOH per volume unit and which was referred to as 'Base Excess', (BE) (see FIG. 4 and appendix 2D). A negative BE exists when the original BE needed for dissolving the C-peptide is over-compensated by addition of a greater amount of HCl-equivalents.

The titration curve was prepared from two formulations (F219-01-001p076, -p098) that were prepared on two different days according to the same procedure and, consequently, could be compared with each other. It can be seen that both curves overlap. This implies that the described standard dissolving method can be used for accurately reproducing C-peptide solutions with a desired pH.

Conclusions

The solubility of C-peptide depends strongly on the actual pH.

A 30 mg/mL C-peptide solution in WFI can be made when the pH of the solution is at least pH 5.2±0.1; C-peptide precipitates at lower pH.

By means of the titration curve of C-peptide, it is possible to accurately reproduce C-peptide solutions with a desired pH.

EXAMPLE 4

C-Peptide Formulations Based on a Low pH

Introduction

The experiments as described in Example 3 show that C-peptide forms a gel of its own when the pH of the solution gets below pH 5.1±0.1. In this Example the gellation process due to a decrease of pH is described in more detail.

Effect of pH on the Formulation

A series of formulations (LJ219-01-001p076A-Q) was prepared by adding appropriate amounts of HCl-equivalents to a 30 mg/mL C-peptide solution of pH 5.15 (see appendix 2D). The pH of the formulations that were obtained varied from pH 1.22 to pH 5.15. At the moment of addition of the HCl white flocks appeared, proportional to the amount of HCl equivalents. The appearances of the formulations in time was followed. The results are summarised in Table 3.

TABLE 3

Overview of the appearances of pH-based C-peptide formulations in time. Gel formation is indicated as 0: liquid, 1: gellous liquid, 2: unstable gel, 3: gel, reversible, 4: stiff gel, disrupted, 5: stiff gel, not disrupted by shear.

| Formulation LJ219-01- | C-peptide conc. | | Appearance Time [days] | | | | |
|---|---|---|---|---|---|---|---|
| 001p076 | mg/mL | pH | 0.125 | 1 | 2 | 5 | 7 | 12 |
| A | 27.3 | 1.22 | 2 | 4 | 4 | 5 | 5 | 5 |
| B | 26.5 | 1.72 | 2 | 4 | 4 | 5 | 5 | 5 |
| C | 26.9 | 1.96 | 2 | 4 | 4 | 5 | 5 | 5 |
| D | 27.3 | 2.25 | 2 | 4 | 4 | 5 | 5 | 5 |
| E | 27.5 | 2.61 | 2 | 4 | 4 | 5 | 5 | 5 |
| F | 27.8 | 3.11 | 2 | 4 | 4 | 4 | 4 | 4 |
| G | 28.1 | 3.62 | 2 | 4 | 4 | 4 | 4 | 5 |
| H | 28.3 | 4.02 | 2 | 4 | 4 | 5 | 3 | 5 |
| J | 28.6 | 4.25 | 2 | 4 | 3 | 5 | 5 | 5 |
| K | 28.8 | 4.42 | 2 | 4 | 3 | 5 | 5 | 5 |
| L | 29.1 | 4.67 | 2 | 2 | 3 | 3 | 3 | 0 |
| M | 27.3 | 4.77 | 2 | 2 | 0 | 3 | 3 | 0 |
| N | 28.1 | 4.83 | 2 | 2 | 0 | 0 | 0 | 0 |
| O | 28.7 | 4.89 | 2 | 2 | 0 | 0 | 0 | 0 |
| P (blank) | 27.8 | 5.14 | 0 | 0 | 0 | 0 | 0 | 0 |
| Q (C-peptide) | 30.0 | 5.15 | 0 | 0 | 0 | 0 | 0 | 0 |

Within 3 hours (0.125 days) most of the formulations (LJ219-01-001p076A-0) had formed gels. Only the blanks (LJ219-01-001p076P,Q) had not formed gels. The higher the HCl content of the formulation (the lower the pH), the denser the precipitate and the stiffer the gel that had been formed. These results were in accordance with previous observations concerning zinc containing gels (see e.g. Examples 1 and 2). However, the gels were not very solid yet. They could easily be transformed back into the liquid state by applying little shear, i.e. gently swirling of, or ticking against, the tube.

After 1 day most formulations at lower pH (LJ219-01-001p076A-K, pH 1.22-4.42) had formed stiff gels, which could only be liquefied by applying higher shear, i.e. mixing on a Vortex mixer at maximum speed (2500 rpm). The formulations at higher pH (LJ219-01-001p076L-O, pH 4.67-4.89) still needed only little shear for becoming liquefied.

The formulations with pH≥4.0 (LJ219-01-001p076H-Q) were reproduced (see appendix 2E) and stored both at ambient temperature (LJ219-01-001p098AN) and at 37° C. (LJ219-01-001p098O-W). The results are summarised in Table. These formulations showed the same results as the previously described formulations (LJ219-01-001p076A-Q).

TABLE 4

Overview of the effect of storage temperature on the appearances of C-peptide in time. Gel formation is indicated as 0: liquid, 1: gellous liquid, 2: unstable gel, 3: gel, reversible, 4: stiff gel, disrupted, 5: stiff gel, not disrupted by shear.

| Formulation | C-peptide conc. | NaOH-excess | | Storage temp | Appearance Time [days] | | |
|---|---|---|---|---|---|---|---|
| LJ219-01-001p098 | Mg/ml | µeq | pH | °C. | 4 | 6 | 35 |
| A | 28.5 | 5.3 | 4.10 | RT | 4 | 4 | 5 |
| B | 28.6 | 7.3 | 4.22 | RT | 4 | 5 | 5 |
| C | 28.8 | 9.8 | 4.34 | RT | 4 | 5 | 5 |
| D | 29.0 | 12.3 | 4.44 | RT | 4 | 5 | 5 |
| E | 29.2 | 14.8 | 4.59 | RT | 4 | 5 | 5 |
| F | 27.2 | 17.5 | 4.74 | RT | 4 | 4 | 4/5 |
| G | 28.0 | 20.0 | 4.82 | RT | 4 | 4 | 4 |
| H | 28.9 | 22.5 | 4.92 | RT | 4 | 4 | 1 |
| J (blank) | 28.5 | 25.3 | 5.02 | RT | 0 | 0 | 0 |
| K | 28.1 | −0.7 | 3.91 | RT | 4 | 4 | 5 |
| L | 28.6 | 6.8 | 4.34 | RT | 4 | 4 | 5 |
| M | 29.1 | 14.3 | 4.71 | RT | 1 | 4 | 4 |
| N | 28.1 | 20.3 | 5.11 | RT | 0 | 0 | 0 |
| O | 28.5 | 5.3 | see A | 37 | 4 | 5 | 5 |
| P | 28.6 | 7.3 | see B | 37 | 4 | 5 | 5 |
| Q | 28.8 | 9.8 | see C | 37 | 4/5 | 5 | 5 |
| R | 29.0 | 12.3 | see D | 37 | 4 | 3 | 5 |
| S | 29.2 | 14.8 | see E | 37 | 4 | 3 | 0 |
| T | 27.2 | 17.5 | see F | 37 | 2 | 3 | 0 |
| U | 28.0 | 20.0 | see G | 37 | 2 | 3 | 0 |
| V | 28.9 | 22.5 | see H | 37 | 2 | 4 | 0 |
| W (blank) | 28.5 | 25.3 | see J | 37 | 2 | 2 | 1 |

After 5 (LJ219-01-001p076A-K) or 6 (LJ219-01-001p098A-H, -p098K-M, -p098O-Q) days the most acidic formulations (pH 1.22-4.59) had formed stiff gels that could not, or hardly (LJ219-01-001p076F-G, LJ219-01-001p098F-H, -p098K-M), be liquefied by mixing for several seconds on a Vortex mixer at maximum speed (2500 rpm). These gels remained solid.

The gels of the formulations that were less acidic (LJ219-01-001p076L-Q, LJ219-01-001p098F-J, -p098M-N, -p098T-W, pH 4.67-4.92) could be disrupted by shear. However, some of them (LJ219-01-001p076L-M, LJ219-01-001p098R-U) showed thixotropic behaviour: they became liquefied by applying shear and then solidified again when left standing, sometimes immediately after being released from the shear source. However, after 7 days this phenomenon was not observed anymore; these samples had become liquids and did not turn into a gel anymore. Therefore, it was assumed that this phenomenon was a result of an increase of pH over time due to $CO_2$ uptake from the air.

The formulation at pH 5.11 (LJ219-01-001p098N) and the blanks (LJ219-01-001p076P-Q, LJ219-01-001p098J) did not show any gel formation at all. However, the blank stored at 37° C. (LJ219-01-001p098W) also formed an unstable gel. This formulation was prepared in exactly the same way as formulation LJ219-01-001p098J but the pH after the preparation was not measured. The pH might have been slightly lower than the pH of formulation LJ219-01-001p098J, through which it just passed the limit of gel formation.

Figure 5:
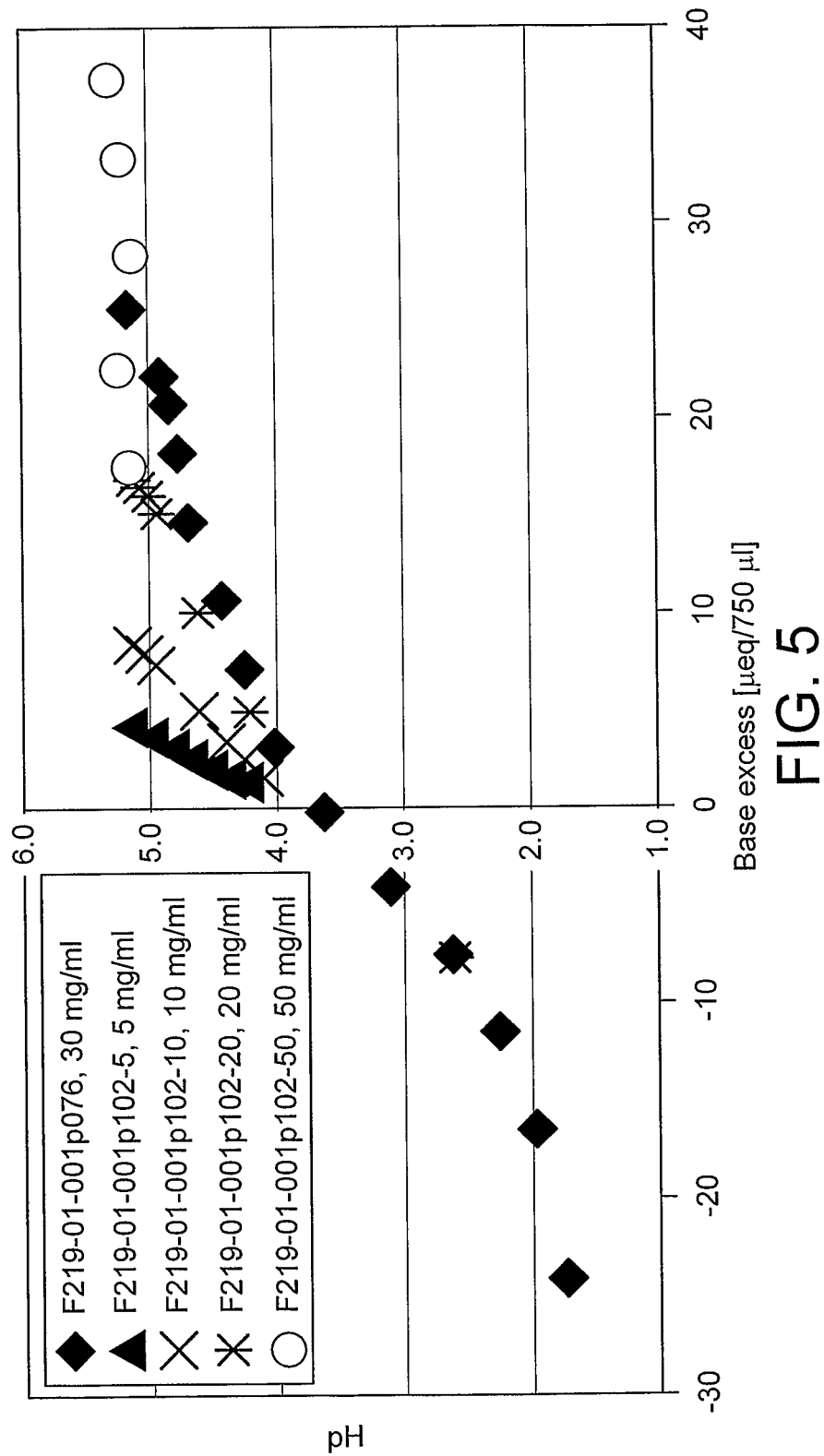
FIG. 5 is a graph showing pH as a function of Base Excess in formulations with different C-peptide concentrations. Formulation F219-01-001p076 (30 mg/mL) is the reference. ♦F219-01-001p076, 30 mg/mL, ▲F219-01-001p102-5, 5 mg/mL, XF219-01-001p102-10, 10 mg/mL, *F219-01-001p102-20, 20 mg/mL, ○F219-01-011p102-50, 50 mg/mL.

As shown in Table 3 there seems to be a trend that gels liquefy spontaneously in time (6 visual inspections in 12 days), the less acidic gels first. However, the results in Table 4 did not endorse these findings (3 visual inspections in 35 days). The number of visual inspections, and with that the number of disturbances of the unstable gels and the inclusion of air (i.e. $CO_2$), might have caused the disruption of the gels.
Effect of a Temperature of 37° C. on the Formulations After administration of a suitable gel formulation subcutaneously, the temperature of the gel will become 37° C. To investigate the effect of T=37° C. on the gel formation, a series of formulations with a pH-range from pH 4.10-4.92 was prepared in duplicate (see Appendix 2E). As a control, one set of formulations was stored at ambient temperature (RT, LJ219-01-001p098A-H), the other set at 37° C. (LJ219-01-001p098O-V) for up to 35 days (see Table 4). It can be seen that the formulations stored at 37° C. were, in general, less solid than those stored at RT. After an incubation of 35 days at 37° C. only the most acidic formulations (LJ219-01-001p098O-R, pH 4.10-4.44) were still solid gels, the other ones had been liquefied. At RT, however, only formulation LJ219-01-001p098H had been liquefied after 35 days. Gels stored at body temperature are less stable than those stored at RT.
Effect of the C-Peptide Concentration on Gel Formation The effect of the C-peptide concentration on gel formation was investigated in combination with a distribution of pH by preparing formulations of different C-peptide concentrations (5, 10, 20, 50 mg/mL) and pH's and observing their appearance in time (see Appendix 2F, Table 5 and FIG. 5).

TABLE 5

Overview of the effect of the C-peptide concentration on the appearances of C-peptide solutions in time. Gel formation is indicated as 0: liquid, 1: gellous liquid, 2: unstable gel, 3: gel, reversible, 4: stiff gel, disrupted, 5: stiff gel, not disrupted by shear.

| Formulation | C-peptide concentration | pH | Appearance Time [days] | | |
|---|---|---|---|---|---|
| LJ219-01-001p102 | mg/mL | — | 3 | 5 | 35 |
| 5 mg/ml | | | | | |
| 5A | 5.0 | 4.99 | 0 | 0 | 0 |
| 5B | 4.9 | 4.82 | 0 | 0 | 0 |
| 5C | 4.9 | 4.67 | 0 | 0 | 0 |
| 5D | 4.9 | 4.53 | 0 | 0 | 0 |
| 5E | 4.8 | 4.38 | 0 | 0 | 0 |
| 5F | 4.8 | 4.24 | 0 | 0 | 2 |
| 5G (=blank) | 5.0 | 5.16 | 0 | 0 | 0 |
| 10 mg/ml | | | | | |
| 10A | 9.9 | 5.04 | 0 | 0 | 0 |
| 10B | 9.9 | 4.95 | 0 | 0 | 0 |
| 10C | 9.6 | 4.60 | 0 | 0 | 2 |

TABLE 5-continued

Overview of the effect of the C-peptide concentration on the appearances of C-peptide solutions in time. Gel formation is indicated as 0: liquid, 1: gellous liquid, 2: unstable gel, 3: gel, reversible, 4: stiff gel, disrupted, 5: stiff gel, not disrupted by shear.

| Formulation | C-peptide concentration | pH | Appearance Time [days] | | |
|---|---|---|---|---|---|
| LJ219-01-001p102 | mg/mL | — | 3 | 5 | 35 |
| 10D | 9.4 | 4.39 | 0 | 1 | 2 |
| 10E | 9.3 | 4.24 | 0 | 2 | 2 |
| 10F | 9.1 | 4.09 | 0 | 0 | 2 |
| 10G (=blank) | 10.0 | 5.12 | 0 | 0 | 0 |
| 20 mg/ml | | | | | |
| 20A | 19.9 | 5.06 | 0 | 0 | 0 |
| 20B | 19.7 | 4.98 | 0 | 0 | 0 |
| 20C | 19.5 | 4.93 | 0 | 0 | 0 |
| 20D | 18.3 | 4.61 | 2 | 2 | 2 |
| 20E | 19.4 | 4.20 | 0 | 1 | 5 |
| 20F | 18.8 | 2.60 | 2 | 0 | 4 |
| 20G (=blank) | 20.0 | 5.10 | 0 | 0 | 0 |
| 50 mg/ml | | | | | |
| 50A | 49.5 | 5.19 | 4 | 3 | 1 |
| 50B | 48.8 | 5.11 | 4 | 3 | 1 |
| 50C | 48.1 | 5.21 | 5 | 5 | 5 |
| 50D | 47.5 | 5.13 | 5 | 5 | 5 |
| 50E (=blank) | 50.0 | 5.27 | 4 | 0 | 0 |

It appeared that the basic parts of the titration curves of the gels with lower C-peptide concentrations (5, 10, 20 mg/mL) laid at higher pH levels than the curves of the gels with a concentration of 30 mg/mL. As predicted, the level of the titration curve is concentration dependent. Gel formation in the low concentrations started after 5 weeks; the formulations with the lowest pH first.

At 50 mg/mL, it appeared that the accuracy of the pH measurement scattered, probably due to the high viscosity of the solutions. That can be the reason why its titration curve laid at, or above, the level of the curve at 30 mg/mL.
Study on the Release of C-Peptide from pH-Based Gel
Mercodia C-Peptide Elisa Specific Kit Samples from release studies were analysed with the Mercodia C-peptide Elisa Specific kit, which provides a method for the quantitative determination of human C-peptide in human body fluids. It is based on a direct sandwich technique in which two monoclonal antibodies are directed against separate antigenic determinants on the C-peptide molecule. During a first incubation step C-peptide from the sample reacts with anti C-peptide antibodies bound to the wall of the micro titration well. After washing, peroxidase-conjugated anti C-peptide antibodies are added and after the second incubation and a simple washing step that removes unbound enzyme labelled antibody, the bound conjugate is detected by reaction with 3,3',5,5'-tetramethylbenzidine (TMB). The reaction is stopped by adding acid to give a colorimetric endpoint that is read spectrophotometrically by a Micro titer plate reader. The results were processed using a cubic spline (log–log) calculation.

At first a number of gels that were based on low pH (F219-01-001p076A-O, see Appendix 2D and Table 2) were immersed in 1.5 mL 500 mM phosphate buffer, pH 7.2. It appeared that the unstable gel (F219-01-001p076F) and the turbid liquids (F219-01-001p076L-O) dissolved in the buffer immediately while the stable gels (F219-01-001p076A-E, -p076G-K) dissolved in the buffer completely within 2 hours. All solutions were clear but contained a fine white precipitate of $Ca_3(PO_4)_2$.

To study this phenomenon more thoroughly, four 30 mg/mL C-peptide formulations with varying pH's were prepared (F219-01-001p128A-D, pH 2.48-4.61, see Table 6). These formulations had become stiff gels and after three weeks the formulations with the lowest pH (F219-01-001p128A, pH 2.48) and the highest pH (F219-01-001p128D, pH 4.61) were selected for the first release study. The other formulations were not sampled while awaiting the results of the Elisa analyses of the experiments.

TABLE 6

Characteristics of 4 C-peptide formulations for release studies

| Formulation | C-peptide concentration [mg/mL] | pH |
|---|---|---|
| F219-01-001p128A | 28.6 | 2.48 |
| F219-01-001p128B | 28.0 | 3.72 |
| F219-01-001p128C | 28.6 | 4.25 |
| F219-01-001p128D | 29.1 | 4.61 |

For this study, to each tube that contained 1 mL gel, 1 mL of a 500 mM phosphate buffer, pH 7.2 was brought on top of the gel, so that one-dimensional diffusion into the gel could take place. Every time that the volume of the gel in the tube had decreased ±15 or 20%, the liquid was poured over into an empty Eppendorf tube and the point of time was noted. Directly after each sampling, another 1 mL of the buffer was added to the tube. The weight of the gel containing tube was measured before and after each sampling, so that a correction for the gel volume could take place after analysis of the samples.

Figure 6:
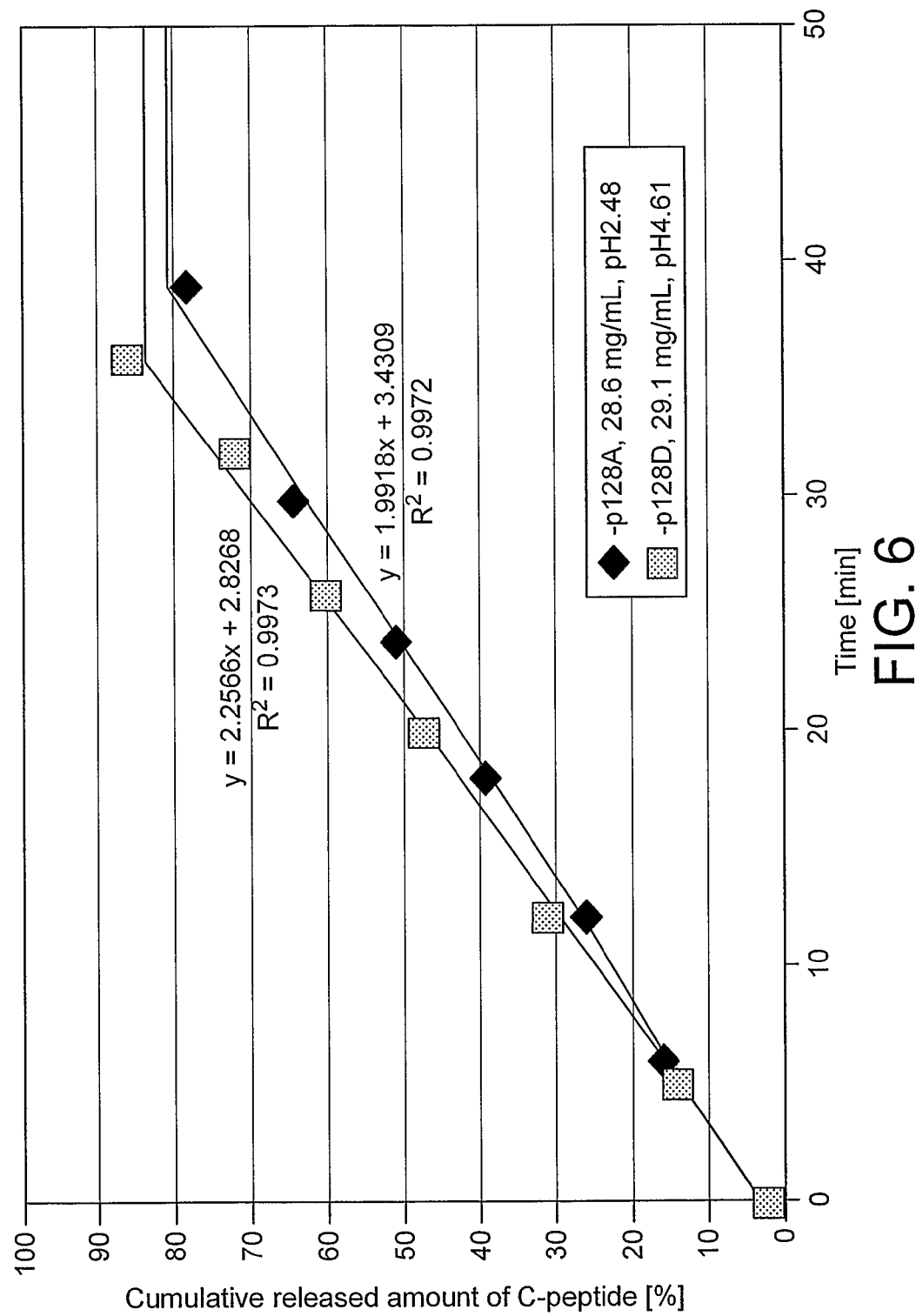
FIG. 6 is a graph showing cumulative C-peptide release from pH based gels (cumulative released amount of C-peptide [%] vs time [min]). The amounts are relative to the total C-peptide amount in the formulation. After the last measuring point the gel was dissolved completely. ♦-p128A, 28.6 mg/mL, pH2.48, □-128D, 29.1 mg/mL, pH4.61.

The gel with the lowest pH (F219-01-001p128A, pH 2.48) dissolved completely in 39 minutes; it took the gel with the highest pH (F219-01-001p128D, pH 4.61) 36 minutes to dissolve completely. Of each formulation, seven release samples were collected over time. All samples were analysed on C-peptide concentration, using the Mercodia C-peptide Elisa Specific kit. The results were corrected for the gel volume. The amounts are relative to the total C-peptide amount in the formulation and shown in FIG. 6. It can be seen from the cumulative results that, in both cases, there was a linear release of C-peptide from the gel in time. However, the recoveries of both analyses are 79.0% (F219-01-001p128A) and 86.3% (F219-01-001p128D), respectively. The low recoveries are not clearly understood.

The difference between both release profiles was smaller than 10%. That indicates that there is hardly any effect of the pH (between pH 2.81 and 4.61). Hence, it was not necessary to analyse the other two formulations with intermediate pH's as well.

Conclusions

The solubility and gel formation abilities of C-peptide depend strongly on its concentration and the actual pH.

At higher pH a slower gel formation occurs while the gels are clearer and show more extensive thixotropic behaviour than at lower pH; however, if the pH becomes too high, no gel formation occurs at all.

Formulations that are stored at 37° C. are less solid than those stored at RT.

The pH induced gels dissolved into a physiological buffer at RT completely within 39 minutes.

The release of C-peptide from the gel in time is linear. Hardly any effect of pH was observed.

EXAMPLE 5

C-Peptide Formulations Based on Zinc Chloride

Introduction

Examples 1 and 2 showed that C-peptide gels could be formed after addition of zinc-ions. However, it took several days before the gel formed and the gel was sensitive to shear.

Preparation of C-Peptide Solutions with Varying pH's

A 36.6 mg/mL C-peptide solution was prepared according to the method as described in Example 3. For every formulation 615 µl of this solution was diluted with 135 µl WFI or a diluted NaOH solution. In this way amounts of 750 µl of a 30 mg/mL C-peptide solution were obtained, of which the pH could be adjusted beforehand (see appendix 2A).

Reproduction of the Formulations as Described in Examples 1 and 2

The first series of formulations (LJ219-01-001p034A-D in Table) was a reproduction of a series that had already been formulated by Creative Peptides; it was based on increasing amounts of a 200 mg/mL $ZnCl_2$ solution that was added to the 750 µl C-peptide solution.

It was noticed that, immediately after the addition of the $ZnCl_2$ solution, white flocks were formed in the C-peptide solutions. The amount of flocks seemed to be proportional to the amount of $ZnCl_2$ added. Formation of flocks was also observed after the addition of HCl to a C-peptide solution (see Example 4).

In time, the flocks piled up to an opaque, gellous mass under a clear liquid. Little shear was needed for breaking the flocks apart. Slowly the white mass became stiffer and the liquid film on top became incorporated into the mass. After 9 days the gels could not be disrupted by shear (Vortex mixer, 2500 rpm) anymore and nothing changed until the end of the experiment after 10 weeks.

TABLE 7

Overview of the effect of zinc and temperature on the appearance of C-peptide solutions in time. Gel formation is indicated as 0: liquid, 1: gelleous liquid, 2: unstable gel, 3: gel, reversible, 4: stiff gel, disrupted, 5: stiff gel, not disrupted by shear.

| Formulation LJ219-01-001p034 | C-peptide Conc. mg/ml | Molar ratio Zn/C-peptide | pH | Storage temp °C. | Appearance Time point [days] | | | | | | | | | | |
|---|---|---|---|---|---|---|---|---|---|---|---|---|---|---|---|
| | | | | | 0 | 1 | 2 | 5 | 9 | 14 | 21 | 28 | 35 | 63 | 70 |
| A | 29.2 | 3.9 | 4.94 | RT | 0 | 1 | 1 | 2 | 4 | 5 | 5 | 5 | 5 | 5 | 5 |
| B | 28.1 | 9.8 | 4.77 | RT | 0 | 1 | 1 | 2 | 5 | 5 | 5 | 5 | 5 | 5 | 5 |

TABLE 7-continued

Overview of the effect of zinc and temperature on the appearance of C-peptide solutions in time. Gel formation is indicated as 0: liquid, 1: gelleous liquid, 2: unstable gel, 3: gel, reversible, 4: stiff gel, disrupted, 5: stiff gel, not disrupted by shear.

| Formulation LJ219-01-001p034 | C-peptide Conc. mg/ml | Molar ratio Zn/C-peptide | pH | Storage temp °C. | Appearance Time point [days] | | | | | | | | | | |
|---|---|---|---|---|---|---|---|---|---|---|---|---|---|---|---|
| | | | | | 0 | 1 | 2 | 5 | 9 | 14 | 21 | 28 | 35 | 63 | 70 |
| C | 27.4 | 13.8 | 4.70 | RT | 0 | 1 | 1 | 2 | 5 | 5 | 5 | 5 | 5 | 5 | 5 |
| D | 26.5 | 19.7 | 4.63 | RT | 0 | 1 | 1 | 2 | 5 | 5 | 5 | 5 | 5 | 5 | 5 |
| E | 26.5 | 19.7 | 4.59 | RT | 0 | 1 | 1 | 1/2 | 5 | 5 | 5 | 5 | 5 | 5 | 5 |
| F | 26.5 | 19.7 | 4.72 | RT | 0 | 1 | 1 | 1/2 | 5 | 5 | 5 | 5 | 5 | 5 | 5 |
| G | 26.5 | 19.7 | 4.97 | RT | 0 | 1 | 1 | 1/2 | 5 | 5 | 5 | 5 | 5 | 5 | 5 |
| H | 26.5 | 19.7 | 5.81 | RT | 0 | 0 | 0 | 0 | 0 | 1 | 5 | 5 | 5 | 5 | 5 |
| L | 26.5 | 19.7 | 6.21 | RT | 0 | 0 | — | 0 | 0 | 0 | 1 | 0 | 4 | 5 | 4 |
| M | 26.5 | 19.7 | 6.27 | RT | 0 | 0 | — | 0 | 0 | 0 | 0 | 5 | 5 | 5 | 5 |
| N | 26.5 | 19.7 | 6.39 | RT | 0 | 0 | — | 0 | 0 | 0 | 0 | 0 | 5 | 5 | 5 |
| O | 26.5 | 19.7 | 6.41 | RT | 0 | 0 | — | 0 | 0 | 0 | 0 | 0 | 5 | 5 | 5 |

Preparation of Formulations at Varying pH's

For the following series (LJ219-01-001p034E-H and -p034L-O in Appendix 2A and Table), formulations were obtained by adding 100 μl of the 200 mg/mL $ZnCl_2$ solution to 750 μl of C-peptide solutions with varying pH's. Formulations LJ219-01-001p034E-G also showed the development of the white flocks, the most in the formulation with the lowest pH (formulation LJ219-01-001p034E, pH 4.59). In time, these three formulations behaved similarly as formulations LJ219-01-001p034A-D (see above).

No flocks were observed in formulation LJ219-01-001p034H, which had a pH 5.81. However, after 3 weeks a stiff gel developed which stayed unremained until the end of the experiment after 10 weeks time.

At higher pH (pH 6.21-6.41), formulations LJ219-01-001p034L-O showed the development of a fine, white precipitate in a clear liquid. The precipitate formed a very thin white layer at the bottom of the tube that was easily whirled around by gently swirling of the tube. Formulations without C-peptide but with zinc chloride at various pH showed this phenomenon similarly. Between 4 and 5 weeks after preparation all formulations LJ219-01-001p034L-O had turned into stiff gels.

Study on the Release of C-Peptide from Gels Based on Zinc Chloride

The previous release experiments in Example 4 described the release of C peptide from gels that were formed purely by adjusting of the pH, i.e. adding NaOH and HCl to a C-peptide solution. For this experiment, zinc containing gels were used.

At first, two gels (LJ219-01-001p034A, -p034G, see appendix 2A) were selected, based on zinc concentration and extra amounts of NaOH added. The first gel (LJ219-01-001p034A) had the lowest zinc chloride concentration (5.2 mg/mL) and pH 4.94, the second (LJ219-01-001p034G) had a 'normal' zinc chloride concentration (23.5 mg/mL) and pH 4.97. It appeared that these gels dissolved slowly into a 500 mM phosphate buffer, pH 7.2, while a thin white precipitate was formed. Within 16 hours both gels had dissolved completely.

A selection of four formulations was made, based on different zinc concentrations and extra amounts of NaOH (see appendix 2A: formulations LJ219-01-001p034B, H, N, appendix 2C: formulation LJ219-01-001p063F). Three out of the four gels dissolved in the 500 mM phosphate buffer, pH 7.2, within 120 (LJ219-01-001p034B), 175 (LJ219-01-001p034N), and 300 (LJ219-01-001p034H) minutes, respectively. Over time, 4-6 samples per formulation were taken according to the procedure described in the release experiment in Example 4. The formulation that contained the highest amount of zinc chloride (LJ219-01-001p063H, 42.1 mg/mL) did not dissolve into the buffer, even after 3 days (=4320 minutes) the surface of the gel seemed to be at the same position as when the experiment started. Over time, 6 samples were taken. All formulations showed the thin white precipitate while they slowly dissolved.

The formulations that were used for this release experiment were used during 10 weeks for observing their appearance in time. Therefore, the first sample of each formulation mainly contained C-peptide that had been attached to the wall of the tube above the gel. However, the purpose of this experiment was to study the diffusion of a physiological buffer in gels into one direction, so the obtained values gave falsely higher results.

The C-peptide content of all samples was analysed, using the Mercodia C-peptide Elisa Specific kit. The results were corrected for the gel volume and presented in FIG. 7.

Figure 7:
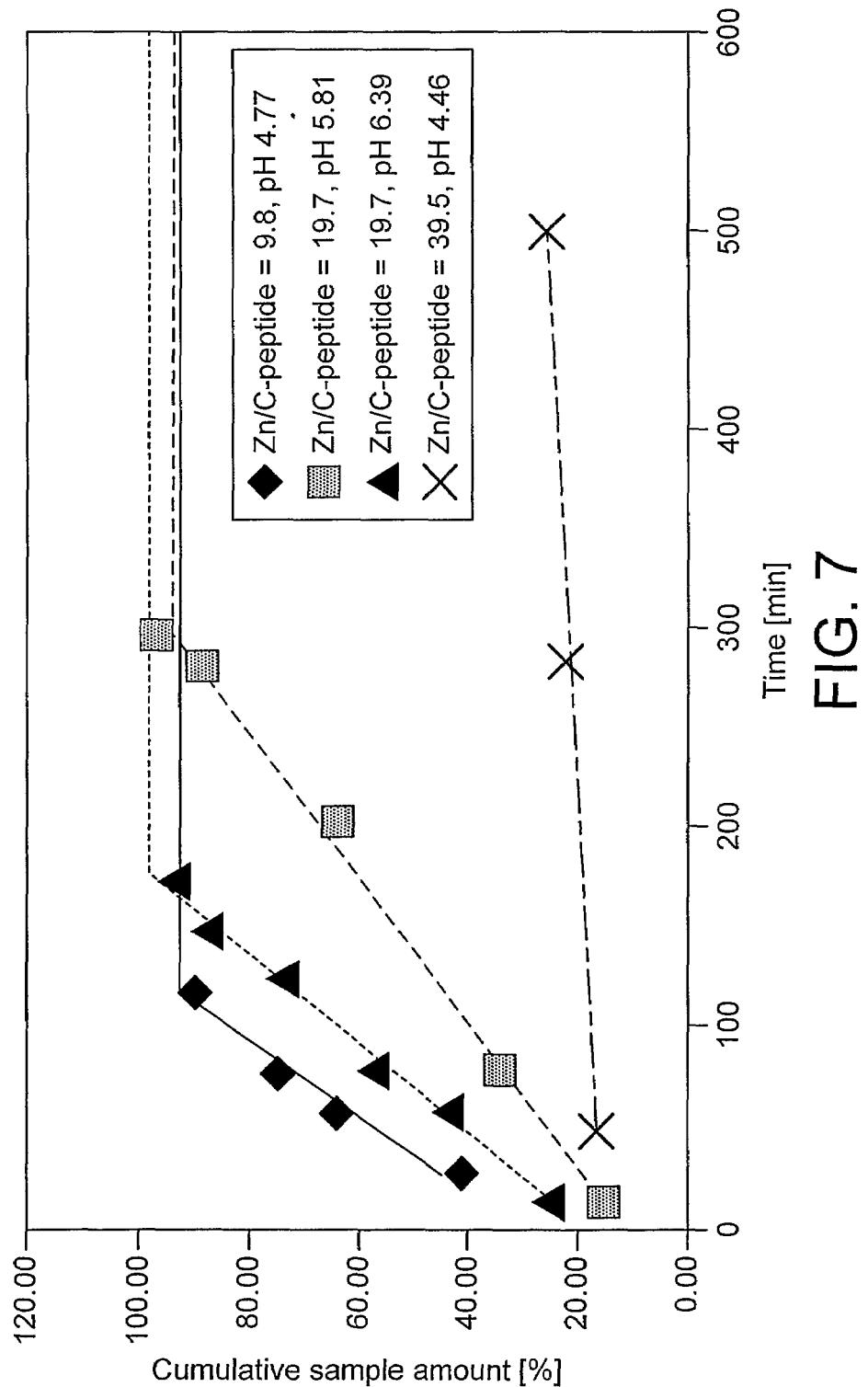
FIG. 7 is a graph showing cumulative C-peptide release from zinc based gels (cumulative sample amount [%] vs Time [min]). The amounts are relative to the total C-peptide amount in the formulation. After the last measuring point the gel was dissolved completely. ♦Zn/C-peptide=9.8, pH 4.77, □Zn/C-peptide=19.7, pH 5.81, ▲Zn/C-peptide=19.7, pH 6.39, XZn/C-peptide=39.5, pH 4.46.

From FIG. 7 it can be seen that, in all cases, there was a linear release of C-peptide from the gels in time due to the linear diffusion of the physiological agent. The main point is that the time scale is much longer (120-300 minutes) than with the formulations based on pH (36-39 minutes, see paragraph 0). The formulation with the highest zinc chloride concentration (LJ219-01-001p063H) released the C-peptide slowly (release >>3 days). During this time span, the C-peptide concentrations of the samples were low (1.37 mg between 50 and 285 minutes, 0.80 mg between 285 and 500 minutes), indicating that very little C-peptide had diffused out of the gel matrix into the buffer.

Discussion

In both formulation series (LJ219-01-001p034A-D, -p034E-H, -p034L-O), as described above, it was noticed that white flocks developed almost immediately after the two solutions had been brought together. This occurred mostly in formulations with the lowest pH's and where the $ZnCl_2$ concentration was relatively high. Measurement of the pH before and after addition of the $ZnCl_2$ solution showed that there was an acidic pH shift due to the addition of this solution. It appeared that the concentrated $ZnCl_2$ solution was acidic from itself. pH 4.0. However, pH shifts of 0.7 pH units (from pH 5.32 to pH 4.63 (LJ219-01-001p034D) and from pH 5.47 to pH 4.72 (LJ219-01-001p034F)) could not be explained just by mixing of the 2 solutions; a chemical reaction must have taken place as well.

On the other hand, if the pH of the formulation became too high, e.g. pH 6.2-6.4 (LJ219-01-001p034L-O), a very fine, white precipitate developed. Formulations without C-peptide at various pH showed the same phenomenon. This indicated that $Zn(OH)_2$ precipitates when the pH becomes higher than 6.11.

After incubation at RT of 9 days, stiff gels were obtained when the pH of the formulation was lower than pH 5 (LJ219-01-001p034B-G). If the pH was higher than pH 5 (LJ219-01-001p034H, -p034L-O) it took 3 to 5 weeks before a solid gel developed.

The purpose of the release experiment was to study the diffusion of a physiological buffer in gels into one direction. However, each first sample of each formulation mainly contained C-peptide that had been attached to the wall of the tube above the gel, so those obtained values were falsely too high. During the release experiments a thin white precipitate developed. Due to the relative high pH (pH 7.2) it must be $Zn_3(PO_4)_2$ that precipitates.

The release of C-peptide from the gels seems to be strongly dependent on the amount of zinc ions incorporated in the gel. The formulation with the highest zinc chloride concentration (LJ219-01-001p063F) released C-peptide hardly. The concentrations were extremely low, which indicated that no C-peptide had diffused into the opposite direction: from the gel into the buffer. This meant that all C-peptide that got released was brought into the solution by degradation of the gel only, and not by diffusion of C-peptide from the gel into the buffer. The effect of the pH seems of minor importance.

In contrast to the low recovery (79.0, 86.3%) of C-peptide from release studies on pH based gels (see paragraph 0) the release of C-peptide from zinc based gels was higher: 90.2% (LJ219-01-001p034B), 96.9% (LJ219-01-001p034H) and 94.2% (LJ219-01-001p034N), respectively.

Conclusions

The addition of the $ZnCl_2$ solution to the C-peptide solution leads to an acidic pH-shift, through which C-peptide flocks out if the pH becomes lower than pH 5.0. Clear formulations are obtained when the pH of the formulation is higher than pH 5.3. If the pH becomes higher than pH 6.11 $Zn(OH)_2$ precipitates.

C-peptide formulations based on zinc ions develop solid gels after some time, varying from days if the pH is below pH 5 until weeks at higher pH.

C-peptide releases linearly from the gels in time. The time scale in which the gel dissolves completely in the physiological agent increases severely with the zinc content and, at a minor scale, with the acidity of the gel. The gels based on pH showed a faster release profile compared to the Zn-containing gels (36-39 minutes and 120-300 minutes, respectively).

The release of C-peptide from the gel is proportional to the dissolution rate of the gel in a physiological agent.

The recovery of C-peptide from the gels was higher than 90%.

EXAMPLE 6

Subcutaneous Administration of C-Peptide in Rats

C-peptide solutions, 20.3 mg/g and 30.0 mg/g, were prepared in the following way. C-peptide, as acetate salt, from PolyPeptide Laboratories GmbH, Germany (PPL 112, batch no 1013/8), was suspended in membrane-filtered water using a magnetic stirrer. The pH was then adjusted to 5-6 by dropwise addition of 10% NaOH (aq.) during stirring at room temperature. A clear solution was obtained after less than 1 h. A zinc chloride solution was prepared by dissolving the salt in membrane-filtered water.

Five samples of C-peptide and zinc chloride mixtures in aqueous solution were prepared in glass tubes by weighing. The mixtures were thoroughly shaken on a vortex mixer and then allowed to stand at room temperature for three weeks in order to be transformed to gels. The appearances of the samples were noted and the results are presented in Table 8.

TABLE 8

Samples for animal tests based on 20.3 mg/g or 30.0 mg/g C-peptide solution

| No | C-peptide (20.3 mg/g) | C-peptide (30.0 mg/g) | $ZnCl_2$ (201 mg/g) | Amount of C-peptide/g | Amount of $ZnCl_2$/g | Molar ratio $Zn^{2+}$:C-peptide | pH | Appearance after 3 weeks at RT |
|---|---|---|---|---|---|---|---|---|
| 1 | 1.8759 g | | 0.1468 g | 18.8 mg | 14.6 mg | 17.2 | 5-6 | Slightly opaque gel |
| 2 | 1.7533 g | | 0.2609 g | 17.7 mg | 26.0 mg | 32.6 | 5-6 | Slightly opaque gel |
| 3 | 1.6454 g | | 0.4406 g | 16.0 mg | 42.5 mg | 58.8 | 5-6 | Almost clear gel |
| 4 | | 1.8273 g | 0.1474 g | 27.8 mg | 15.0 mg | 12.0 | 5 | Slightly opaque gel |
| 5 | | 1.7541 g | 0.2598 g | 26.1 mg | 25.9 mg | 22.0 | 5 | Opaque gel |

About 1 ml of each sample was transferred to a plastic syringe with a Luer-lok Tip (Becton Dickinson), which then was sealed with a Combi Stopper (Braun). Prior to administration a 23G Microlance (Becton Dickinson) was connected to the syringe. Each syringe was weighed before and after administration to the animal.

Thirty Sprague-Dawley male rats with a body weight of about 300 g were divided into 5 groups of 6 animals to test the uptake of C-peptide in the formulations outlined above. The formulations were administered subcutaneously (about 100 µl, corresponding to about 21 mole/kg) and 300 µl blood samples were taken in serum test tubes from the tail-vein at 0.5, 1, 3, 5, 7, and 24 h after administration of the formulation. The serum obtained by centrifugation was collected and stored at −80° C. until analysis. Determination of C-peptide in serum was performed by an automatic immunoassay system (AutoDELFIA™ C-peptide, Perkin Elmer, Wallac Oy, Turku, Finland), with a detection limit of 0.005 nM and a precision below 5%. To fit into the calibration curve, the samples were diluted prior to analysis 100 times.

Figure 8:
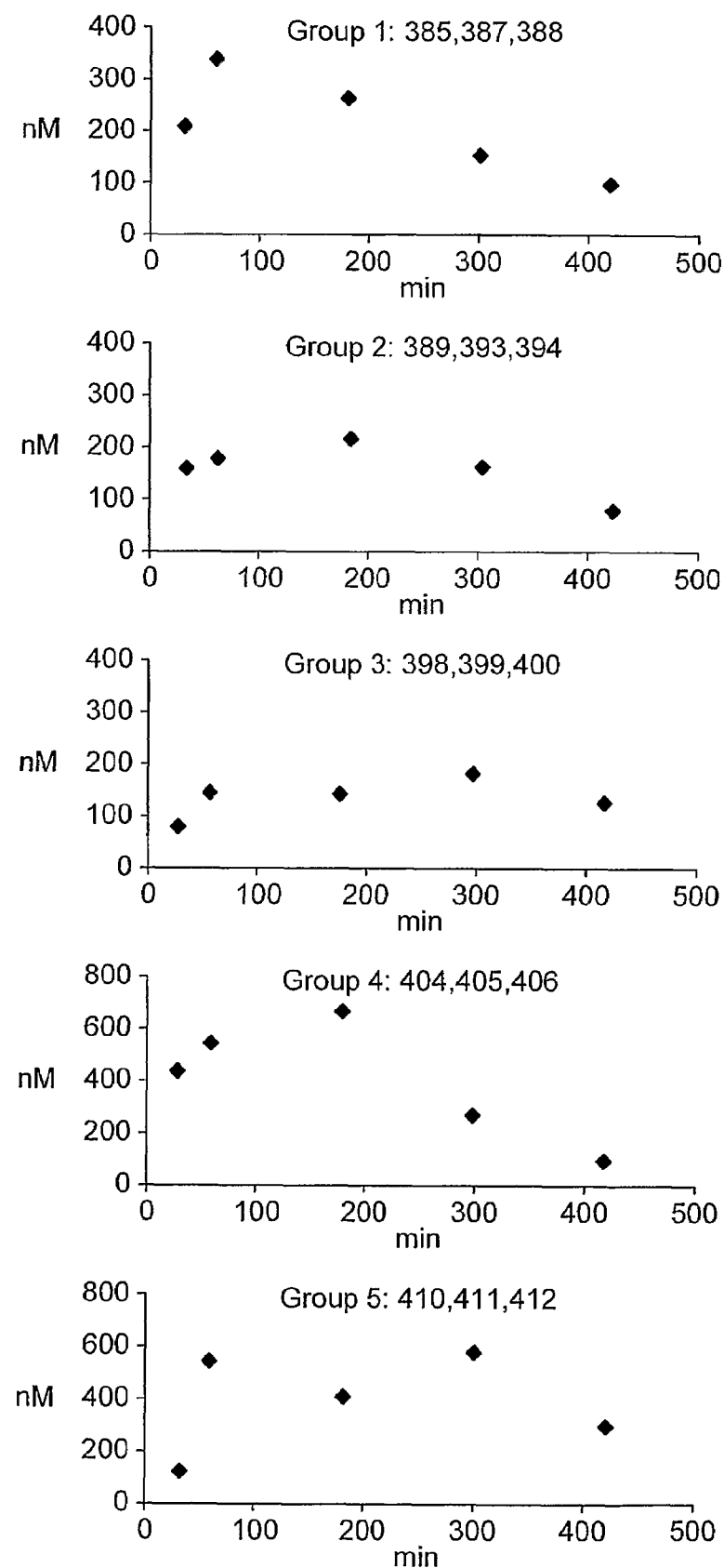
FIG. 8 presents five graphs showing the average C-peptide content in serum versus time after subcutaneous administration of different C-peptide gel formulations with zinc in rats (n=3 in each group). The numbers in the headings of each graph represent the individual animals that were used in the tests.

The results are presented in FIG. 8. Due to phase separation (release of water) during and after the transfer of the formulations from the glass containers to the syringes, data for two animals in each group had to be removed (unreasonably low serum concentrations). Thus, the data presented in FIG. 8 are average concentrations for three animals in each group. Each group of animals exhibits high levels of C-peptide in serum, which extend for more than about 400 min, with higher levels for the two groups that were given the highest doses (Group 4 and 5). No C-peptide could be detected in serum at 24 h (data points not shown).

On the other hand, if C-peptide is given subcutaneously to rats (75 nmole/kg) as a common aqueous solution, a much faster decrease in serum concentration is observed (below 1 nM within 2 h; data not shown). This indicates that the C-peptide gels according to the present invention provide for a sustained release in vivo.

No adverse effects were observed during the administration of the formulations to the rats.

Appendix 2A

Preparation of formulations F219-01-001p034 (variables in pH and storage temperature).

| Formulation LJ219-01-001p034 | C-peptide | | | | | | Cation | | | Total Volume μL | End pH |
|---|---|---|---|---|---|---|---|---|---|---|---|
| | 0.25 M Volume μL | NaOH μL | WFI μL | Total volume μL | Conc. mg/mL | pH | Type | Volume μL | Conc. mg/g | | |
| A | 615 | — | 135 | 750 | 30 | — | Zn | 20 | 200 | 770.00 | 4.94 |
| B | 615 | — | 135 | 750 | 30 | — | Zn | 50 | 200 | 800.00 | 4.77 |
| C | 615 | — | 135 | 750 | 30 | — | Zn | 70 | 200 | 820.00 | 4.70 |
| D | 615 | — | 135 | 750 | 30 | 5.32 | Zn | 100 | 200 | 850.00 | 4.63 |
| E | 615 | 0 | 135 | 750 | 30 | — | Zn | 100 | 200 | 850.00 | 4.59 |
| F | 615 | 5 | 130 | 750 | 30 | 5.47 | Zn | 100 | 200 | 850.00 | 4.72 |
| G | 615 | 15 | 120 | 750 | 30 | — | Zn | 100 | 200 | 850.00 | 4.97 |
| H | 615 | 35 | 100 | 750 | 30 | — | Zn | 100 | 200 | 850.00 | 5.81 |
| J | 615 | — | 135 | 750 | 30 | — | Ca | 100 | 216 | 850.00 | 4.82 |
| K | 750 | N.A. | N.A. | 750 | 50 | 5.25 | — | — | — | N.A. | N.A. |
| L | 615 | 50 | 85 | 750 | 30 | — | Zn | 100 | 200 | 850.00 | 6.21 |
| M | 615 | 70 | 65 | 750 | 30 | — | Zn | 100 | 200 | 850.00 | 6.27 |
| N | 615 | 90 | 45 | 750 | 30 | — | Zn | 100 | 200 | 850.00 | 6.39 |
| O | 615 | 110 | 25 | 750 | 30 | — | Zn | 100 | 200 | 850.00 | 6.41 |

| Formulation LJ219-01-001p034 | C-peptide | | ZnCl2 | | Zn/C-peptide Molar ratio | Storage temp °C |
|---|---|---|---|---|---|---|
| | Conc. mg/mL | Conc. mmol/mL | Conc. mg/mL | Conc. mmol/mL | | |
| A | 29.2 | 0.0097 | 5.2 | 0.0381 | 3.9 | RT |
| B | 28.1 | 0.0093 | 12.5 | 0.0917 | 9.8 | RT |
| C | 27.4 | 0.0091 | 17.1 | 0.1253 | 13.8 | RT |
| D | 26.5 | 0.0088 | 23.5 | 0.1727 | 19.7 | RT |
| E | 26.5 | 0.0088 | 23.5 | 0.1727 | 19.7 | RT |
| F | 26.5 | 0.0088 | 23.5 | 0.1727 | 19.7 | RT |
| G | 26.5 | 0.0088 | 23.5 | 0.1727 | 19.7 | RT |
| H | 26.5 | 0.0088 | 23.5 | 0.1727 | 19.7 | RT |
| J | 26.5 | 0.0088 | 25.4 | 0.1728 | 19.7 | RT |
| K | N.A. | N.A. | N.A. | N.A. | N.A. | N.A. |
| L | 26.5 | 0.0088 | 23.5 | 0.1727 | 19.7 | RT |
| M | 26.5 | 0.0088 | 23.5 | 0.1727 | 19.7 | RT |
| N | 26.5 | 0.0088 | 23.5 | 0.1727 | 19.7 | RT |
| O | 26.5 | 0.0088 | 23.5 | 0.1727 | 19.7 | RT |

APPENDIX 2C

Preparation of formulations F219-01-001p063.

| Formulation LJ219-01-001p063 | C-peptide | | | | | Cation | | | Total Volume μL | End pH | C-peptide | | Cation | Cation/C-peptide Molar ratio | Storage temp °C |
|---|---|---|---|---|---|---|---|---|---|---|---|---|---|---|---|
| | Volume μL | WFI μL | Total volume μL | Conc. mg/mL | pH | Type | Volume μL | Conc. mol/L | | | Conc. mg/mL | Conc. mmol/mL | Conc. mmol/mL | | |
| F | 750 | N.A. | 750 | 30 | 5.34 | Zn HCl | 200 | 1.47 | 950 | 4.46 | 23.7 | 0.0078 | 0.31 | 39.5 | RT |
| L | 615 | 135 | 750 | 30 | — | H | 50 | 1.47 | 800 | 1.33 | 28.1 | 0.0093 | 0.09 | 9.9 | RT |
| M | 615 | 135 | 750 | 30 | — | H | 25 | 1.47 | 775 | 2.69 | 29.0 | 0.0096 | 0.05 | 4.9 | RT |

APPENDIX 2C-continued

Preparation of formulations F219-01-001p063.

| Formulation LJ219-01-001p063 | C-peptide Volume μL | WFI μL | Total volume μL | Conc. mg/mL | pH | Type | Volume μL | Conc. mol/L | Total Volume μL | End pH | C-peptide Conc. mg/mL | C-peptide Conc. mmol/mL | Cation Conc. mmol/mL | Cation/C-peptide Molar ratio | Storage temp °C |
|---|---|---|---|---|---|---|---|---|---|---|---|---|---|---|---|
| N | 615 | 135 | 750 | 30 | — | H | 10 | 1.47 | 760 | 4.53 | 29.6 | 0.0098 | 0.02 | 2.0 | RT |
| O | 615 | 135 | 750 | 30 | — | H | 100 | 0.1 | 850 | 4.71 | 26.5 | 0.0088 | 0.01 | 1.3 | RT |
| P (blank) | 615 | 135 | 750 | 30 | — | H | 0 | 0 | 750 | 5.37 | 30.0 | 0.0099 | 0.00 | 0.0 | RT |

APPENDIX 2D

Preparation of formulations F219-01-001p076, based on different Base Excesses and, with that, pH.

| Formulation LJ219-01-001p076 | C-peptide Volume μL | Conc. mg/mL | pH | HCl Volume μL | Conc mol/L | Total Volume μL | End pH | C-peptide Conc mg/mL | C-peptide Conc mmol/mL | HCl Conc mmol/mL | HCl/C-peptide Molar ratio | Storage temp °C | NaOH μeq | HCl μeq | NaOH-excess μeq |
|---|---|---|---|---|---|---|---|---|---|---|---|---|---|---|---|
| A | 750 | 30 | 5.15 | 75 | 1.0 | 825 | 1.22 | 27.3 | 0.0090 | 0.091 | 10.1 | RT | 25.6 | 75.0 | −49.4 |
| B | 750 | 30 | | 100 | 0.5 | 850 | 1.72 | 26.5 | 0.0088 | 0.059 | 6.7 | RT | 25.6 | 50.0 | −24.4 |
| C | 750 | 30 | | 85 | 0.5 | 835 | 1.96 | 26.9 | 0.0089 | 0.051 | 5.7 | RT | 25.6 | 42.5 | −16.9 |
| D | 750 | 30 | | 75 | 0.5 | 825 | 2.25 | 27.3 | 0.0090 | 0.045 | 5.0 | RT | 25.6 | 37.5 | −11.9 |
| E | 750 | 30 | | 67 | 0.5 | 817 | 2.61 | 27.5 | 0.0091 | 0.041 | 4.5 | RT | 25.6 | 33.5 | −7.9 |
| F | 750 | 30 | | 60 | 0.5 | 810 | 3.11 | 27.8 | 0.0092 | 0.037 | 4.0 | RT | 25.6 | 30.0 | −4.4 |
| G | 750 | 30 | | 52 | 0.5 | 802 | 3.62 | 28.1 | 0.0093 | 0.032 | 3.5 | RT | 25.6 | 26.0 | −0.4 |
| H | 750 | 30 | | 45 | 0.5 | 795 | 4.02 | 28.3 | 0.0094 | 0.028 | 3.0 | RT | 25.6 | 22.5 | 3.1 |
| J | 750 | 30 | | 37 | 0.5 | 787 | 4.25 | 28.6 | 0.0095 | 0.024 | 2.5 | RT | 25.6 | 18.5 | 7.1 |
| K | 750 | 30 | | 30 | 0.5 | 780 | 4.42 | 28.8 | 0.0096 | 0.019 | 2.0 | RT | 25.6 | 15.0 | 10.6 |
| L | 750 | 30 | | 22 | 0.5 | 772 | 4.67 | 29.1 | 0.0096 | 0.014 | 1.5 | RT | 25.6 | 11.0 | 14.6 |
| M | 750 | 30 | | 75 | 0.1 | 825 | 4.77 | 27.3 | 0.0090 | 0.009 | 1.0 | RT | 25.6 | 7.5 | 18.1 |
| N | 750 | 30 | | 50 | 0.1 | 800 | 4.83 | 28.1 | 0.0093 | 0.006 | 0.7 | RT | 25.6 | 5.0 | 20.6 |
| O | 750 | 30 | | 35 | 0.1 | 785 | 4.89 | 28.7 | 0.0095 | 0.004 | 0.5 | RT | 25.6 | 3.5 | 22.1 |
| P (blank) | 750 | 30 | | 60 | 0.0 | 810 | 5.14 | 27.8 | 0.0092 | 0.000 | 0.0 | RT | 25.6 | 0.0 | 25.6 |
| Q (C-peptide solution) | 750 | 30 | | 0 | 0.0 | 750 | 5.15 | 30.0 | 0.0099 | 0.000 | 0.0 | RT | 25.6 | 0.0 | 25.6 |

APPENDIX 2E

Preparation of formulations F219-01-001p098, based on different Base Excesses and on temperature.

| Formulation LJ219-01-001p098 | C-peptide Volume μL | Conc. mg/mL | pH | HCl Volume μL | Conc mol/L | Total Volume μL | End pH | C-peptide Conc mg/mL | C-peptide Conc mmol/mL | HCl Conc mmol/mL | HCl/C-peptide Molar ratio | Storage temp °C | NaOH μeq | HCl μeq | NaOH-excess μeq |
|---|---|---|---|---|---|---|---|---|---|---|---|---|---|---|---|
| A | 750 | 30 | 5.12 | 40 | 0.5 | 790 | 4.10 | 28.5 | 0.0094 | 0.025 | 2.7 | RT | 25.3 | 20.0 | 5.3 |
| B | 750 | 30 | | 36 | 0.5 | 786 | 4.22 | 28.6 | 0.0095 | 0.023 | 2.4 | RT | 25.3 | 18.0 | 7.3 |
| C | 750 | 30 | | 31 | 0.5 | 781 | 4.34 | 28.8 | 0.0095 | 0.020 | 2.1 | RT | 25.3 | 15.5 | 9.8 |
| D | 750 | 30 | | 26 | 0.5 | 776 | 4.44 | 29.0 | 0.0096 | 0.017 | 1.7 | RT | 25.3 | 13.0 | 12.3 |
| E | 750 | 30 | | 21 | 0.5 | 771 | 4.59 | 29.2 | 0.0097 | 0.014 | 1.4 | RT | 25.3 | 10.5 | 14.8 |
| F | 750 | 30 | | 78 | 0.1 | 828 | 4.74 | 27.2 | 0.0090 | 0.009 | 1.0 | RT | 25.3 | 7.8 | 17.5 |
| G | 750 | 30 | | 53 | 0.1 | 803 | 4.82 | 28.0 | 0.0093 | 0.007 | 0.7 | RT | 25.3 | 5.3 | 20.0 |
| H | 750 | 30 | | 28 | 0.1 | 778 | 4.92 | 28.9 | 0.0096 | 0.004 | 0.4 | RT | 25.3 | 2.8 | 22.5 |
| J (blank) | 750 | 30 | | 40 | 0.0 | 790 | 5.02 | 28.5 | 0.0094 | 0.000 | 0.0 | RT | 25.3 | 0.0 | 25.3 |
| K | 750 | 30 | | 52 | 0.5 | 802 | 3.91 | 28.1 | 0.0093 | 0.032 | 3.5 | RT | 25.3 | 26.0 | −0.7 |
| L | 750 | 30 | | 37 | 0.5 | 787 | 4.34 | 28.6 | 0.0095 | 0.024 | 2.5 | RT | 25.3 | 18.5 | 6.8 |
| M | 750 | 30 | | 22 | 0.5 | 772 | 4.71 | 29.1 | 0.0096 | 0.014 | 1.5 | RT | 25.3 | 11.0 | 14.3 |
| N | 750 | 30 | | 50 | 0.1 | 800 | 5.11 | 28.1 | 0.0093 | 0.006 | 0.7 | RT | 25.3 | 5.0 | 20.3 |
| O | 750 | 30 | | 40 | 0.5 | 790 | see A | 28.5 | 0.0094 | 0.025 | 2.7 | 37 | 25.3 | 20.0 | 5.3 |
| P | 750 | 30 | | 36 | 0.5 | 786 | see B | 28.6 | 0.0095 | 0.023 | 2.4 | 37 | 25.3 | 18.0 | 7.3 |
| Q | 750 | 30 | | 31 | 0.5 | 781 | see C | 28.8 | 0.0095 | 0.020 | 2.1 | 37 | 25.3 | 15.5 | 9.8 |
| R | 750 | 30 | | 26 | 0.5 | 776 | see D | 29.0 | 0.0096 | 0.017 | 1.7 | 37 | 25.3 | 13.0 | 12.3 |

APPENDIX 2E-continued

Preparation of formulations F219-01-001p098, based on different Base Excesses and on temperature.

| Formulation LJ219-01-001p098 | C-peptide Volume µL | C-peptide Conc. mg/mL | pH | HCl Volume µL | HCl Conc mol/L | Total Volume µL | End pH | C-peptide Conc mg/mL | C-peptide Conc mmol/mL | HCl Conc mmol/mL | HCl/C-peptide Molar ratio | Storage temp °C. | NaOH µeq | HCl µeq | NaOH-excess µeq |
|---|---|---|---|---|---|---|---|---|---|---|---|---|---|---|---|
| S | 750 | 30 | | 21 | 0.5 | 771 | see E | 29.2 | 0.0097 | 0.014 | 1.4 | 37 | 25.3 | 10.5 | 14.8 |
| T | 750 | 30 | | 78 | 0.1 | 828 | see F | 27.2 | 0.0090 | 0.009 | 1.0 | 37 | 25.3 | 7.8 | 17.5 |
| U | 750 | 30 | | 53 | 0.1 | 803 | see G | 28.0 | 0.0093 | 0.007 | 0.7 | 37 | 25.3 | 5.3 | 20.0 |
| V | 750 | 30 | | 28 | 0.1 | 778 | see H | 28.9 | 0.0096 | 0.004 | 0.4 | 37 | 25.3 | 2.8 | 22.5 |
| W (blank) | 750 | 30 | | 40 | 0.0 | 790 | see J | 28.5 | 0.0094 | 0.000 | 0.0 | 37 | 25.3 | 0.0 | 25.3 |

APPENDIX 2F

Preparation of formulations F219-01-001p102, based on different C-peptide concentrations.

| Formulation LJ219-01-001p102 | C-peptide Volume µL | C-peptide Conc. mg/mL | pH | HCl Volume µL | HCl Conc. mol/L | Total Volume µL | End pH | C-peptide Conc. mg/mL | C-peptide Conc. Mmol/mL | HCl Conc. mmol/mL | HCl/C-peptide Molar ratio | Storage temp °C. | NaOH µeq | HCl µeq | NaOH-excess µeq |
|---|---|---|---|---|---|---|---|---|---|---|---|---|---|---|---|
| 5 mg/mL | | | | | | | | | | | | | | | |
| 5A | 750 | 5 | 5.14 | 5 | 0.1 | 755 | 4.99 | 5.0 | 0.0016 | 0.001 | 0.4 | RT | 4.2 | 0.5 | 3.7 |
| 5B | 750 | 5 | | 10 | 0.1 | 760 | 4.82 | 4.9 | 0.0016 | 0.001 | 0.8 | RT | 4.2 | 1.0 | 3.2 |
| 5C | 750 | 5 | | 15 | 0.1 | 765 | 4.67 | 4.9 | 0.0016 | 0.002 | 1.2 | RT | 4.2 | 1.5 | 2.7 |
| 5D | 750 | 5 | | 20 | 0.1 | 770 | 4.53 | 4.9 | 0.0016 | 0.003 | 1.6 | RT | 4.2 | 2.0 | 2.2 |
| 5E | 750 | 5 | | 25 | 0.1 | 775 | 4.38 | 4.8 | 0.0016 | 0.003 | 2.0 | RT | 4.2 | 2.5 | 1.7 |
| 5F | 750 | 5 | | 30 | 0.1 | 780 | 4.24 | 4.8 | 0.0016 | 0.004 | 2.4 | RT | 4.2 | 3.0 | 1.2 |
| 5G (=blank) | 750 | 5 | | 0 | 0.0 | 750 | 5.16 | 5.0 | 0.0017 | 0.000 | 0.0 | RT | 4.2 | 0.0 | 4.2 |
| 10 mg/mL | | | | | | | | | | | | | | | |
| 10A | 750 | 10 | 5.12 | 5 | 0.1 | 755 | 5.04 | 9.9 | 0.0033 | 0.001 | 0.2 | RT | 8.4 | 0.5 | 7.9 |
| 10B | 750 | 10 | | 10 | 0.1 | 760 | 4.95 | 9.9 | 0.0033 | 0.001 | 0.4 | RT | 8.4 | 1.0 | 7.4 |
| 10C | 750 | 10 | | 34 | 0.1 | 784 | 4.60 | 9.6 | 0.0032 | 0.004 | 1.4 | RT | 8.4 | 3.4 | 5.0 |
| 10D | 750 | 10 | | 50 | 0.1 | 800 | 4.39 | 9.4 | 0.0031 | 0.006 | 2.0 | RT | 8.4 | 5.0 | 3.4 |
| 10E | 750 | 10 | | 60 | 0.1 | 810 | 4.24 | 9.3 | 0.0031 | 0.007 | 2.4 | RT | 8.4 | 6.0 | 2.4 |
| 10F | 750 | 10 | | 70 | 0.1 | 820 | 4.09 | 9.1 | 0.0030 | 0.009 | 2.8 | RT | 8.4 | 7.0 | 1.4 |
| 10G (=blank) | 750 | 10 | | 0 | 0.0 | 750 | 5.12 | 10.0 | 0.0033 | 0.000 | 0.0 | RT | 8.4 | 0.0 | 8.4 |
| 20 mg/mL | | | | | | | | | | | | | | | |
| 20A | 750 | 20 | 5.10 | 5 | 0.1 | 755 | 5.06 | 19.9 | 0.0066 | 0.001 | 0.1 | RT | 16.9 | 0.5 | 16.4 |
| 20B | 750 | 20 | | 10 | 0.1 | 760 | 4.98 | 19.7 | 0.0065 | 0.001 | 0.2 | RT | 16.9 | 1.0 | 15.9 |
| 20C | 750 | 20 | | 19 | 0.1 | 769 | 4.93 | 19.5 | 0.0065 | 0.002 | 0.4 | RT | 16.9 | 1.9 | 15.0 |
| 20D | 750 | 20 | | 69 | 0.1 | 819 | 4.61 | 18.3 | 0.0061 | 0.008 | 1.4 | RT | 16.9 | 6.9 | 10.0 |
| 20E | 750 | 20 | | 24 | 0.5 | 774 | 4.20 | 19.4 | 0.0064 | 0.016 | 2.4 | RT | 16.9 | 12.0 | 4.9 |
| 20F | 750 | 20 | | 50 | 0.5 | 800 | 2.60 | 18.8 | 0.0062 | 0.031 | 5.0 | RT | 16.9 | 25.0 | −8.1 |
| 20G (=blank) | 750 | 20 | | 0 | 0.0 | 750 | 5.10 | 20.0 | 0.0066 | 0.000 | 0.0 | RT | 16.9 | 0.0 | 16.9 |
| 50 mg/mL | | | | | | | | | | | | | | | |
| 50A | 750 | 50 | 5.19 | 8 | 0.5 | 758 | 5.19 | 49.5 | 0.0164 | 0.005 | 0.3 | RT | 37.5 | 4.0 | 33.5 |
| 50B | 750 | 50 | | 18 | 0.5 | 768 | 5.11 | 48.8 | 0.0162 | 0.012 | 0.7 | RT | 37.5 | 9.0 | 28.5 |
| 50C | 750 | 50 | | 30 | 0.5 | 780 | 5.21 | 48.1 | 0.0159 | 0.019 | 1.2 | RT | 37.5 | 15.0 | 22.5 |
| 50D | 750 | 50 | | 40 | 0.5 | 790 | 5.13 | 47.5 | 0.0157 | 0.025 | 1.6 | RT | 37.5 | 20.0 | 17.5 |
| 50E (=blank) | 750 | 50 | | 0 | 0.0 | 750 | 5.27 | 50.0 | 0.0166 | 0.000 | 0.0 | RT | 37.5 | 0.0 | 37.5 |

The invention claimed is:

1. A pharmaceutical composition for the sustained release of C-peptide said composition being in the form of a gel comprising colloidal C-peptide,
   wherein said C-peptide is full length as disclosed in SEQ. ID. Nos. 1-24, or a fragment of each one thereof comprising residues 15-31 when at least 31 residues are present, or as disclosed in SEQ. ID. Nos. 25-31,
   wherein gel formation is induced by the adjustment of pH of said composition and/or by addition of divalent metal ions, and
   wherein said composition does not include any gel-forming agents, other than metal ions, if present.

2. The pharmaceutical composition according to claim 1 in the form of a gel comprising colloidal C-peptide and divalent metal ions, wherein said metal ions are the sole gel-forming agent in the composition.

3. A composition comprising colloidal C-peptide and metal ions obtainable by mixing an aqueous solution of C-peptide with an aqueous solution of divalent metal ions and leaving said mixture for a length of time sufficient to form a gel,
   wherein said C-peptide is full length as disclosed in SEQ. ID. Nos. 1-24, or a fragment of each one thereof comprising residues 15-31 when at least 31 residues are present, or as disclosed in SEQ. ID. Nos. 25-31, and
   wherein said metal ions are the sole gel-forming agent in the composition.

4. The composition according to claim 1 or 3 wherein said metal ions are selected from the group consisting of zinc(II), nickel(II), cobalt(II), magnesium, calcium, manganese, iron (II) and copper(II).

5. The composition according to claim 4 wherein said metal ions are provided in the form of a salt.

6. The composition according to claim 5 wherein said metal salt is a chloride, sulphate, phosphate, citrate, acetate, formate and/or a nitrate.

7. The composition according to claim 5 wherein said metal salt is selected from the group consisting of zinc chloride, zinc sulphate, calcium chloride and calcium sulphate.

8. The composition according to claim 1 wherein said pH is adjusted to 4-7.

9. The composition according to claim 8 wherein said pH is adjusted by reducing the pH.

10. The composition according to claim 1 or 3 wherein said C-peptide is present at a concentration from 10 to 50 or 10 to 30 mg/ml.

11. The composition according to claim 1 or 3 wherein said C-peptide is provided in the form of a salt.

12. The composition according to claim 11 wherein said C-peptide is provided as a sulphate, chloride, acetate, phosphate, citrate, formate, nitrate or a carboxylic acid salt.

13. The composition of claim 12 wherein said C-peptide is in the form of an acetate salt.

14. The composition of claim 1 or 3 wherein said gel is thixotropic.

15. The composition of claim 1 or 3 further comprising viscosity-adjusting agents and/or co-solvents which are miscible with water.

16. A method of producing a composition according to claim 1 or 3 in gel form comprising C-peptide, said method comprising the steps of
   (i) mixing an aqueous solution of C-peptide with an aqueous solution of divalent metal ions and
   (ii) leaving the mixture for a length of time sufficient to form a gel.

17. The method of claim 16 wherein the mixture is left for at least 12 hours, 1-6 days or 3-5 days to form a gel.

18. The method of claim 16 wherein said aqueous solution is prepared to be of a predetermined pH or wherein the pH of the C-peptide solution or reaction mixture is adjusted.

19. A method of producing a composition according to claim 1 in gel form comprising C-peptide, said method comprising adjusting the pH of an aqueous C-peptide solution and allowing a gel to form.

20. The method according to claim 19 wherein the pH is reduced to pH 5 or below.

21. A method of combating type I diabetes or diabetic complications of type I diabetes in a patient in need thereof, said method comprising administering to said patient a composition according to claim 1 or 3.

22. A product containing two or more gel compositions as defined in claim 1 or 3 as a combined preparation for simultaneous use in C-peptide based therapy.

23. A product containing a gel composition according to claim 1 or 3, together with a further active agent effective to combat diabetes or diabetic complications as a combined preparation for simultaneous use in combating diabetes and/or diabetic complications.

* * * * *